United States Patent [19]

Ungpiyakul et al.

[11] Patent Number: 5,286,543

[45] Date of Patent: Feb. 15, 1994

[54] METHOD AND APPARATUS FOR CONTROLLING THE CUTTING AND PLACEMENT OF COMPONENTS ON A MOVING SUBSTRATE, AND ARTICLE MADE THEREWITH

[75] Inventors: Tanakon Ungpiyakul, Neenah; Christopher J. Sheleski, Menasha; Arch D. Morgan, Neenah, all of Wis.; Terry G. Hayes, Eden, Utah; Gene M. Gregory, Neenah; Daniel J. Vander Heiden, Appleton, both of Wis.

[73] Assignee: Kimberly-Clark Corporation, Neenah, Wis.

[21] Appl. No.: 59,945

[22] Filed: May 6, 1993

Related U.S. Application Data

[62] Division of Ser. No. 832,511, Feb. 7, 1992, Pat. No. 5,235,515.

[51] Int. Cl.⁵ .................... A61F 13/15; B32B 33/00
[52] U.S. Cl. ........................... 428/74; 428/78; 428/79; 428/195; 428/206; 428/286; 604/385.1
[58] Field of Search ............... 428/74, 78, 79, 195, 428/206, 286; 604/385.1

[56] References Cited

U.S. PATENT DOCUMENTS

| | | | |
|---|---|---|---|
| 4,237,539 | 12/1980 | Piovoso et al. | 364/552 |
| 4,264,957 | 4/1981 | Pautzke | 364/469 |
| 4,449,433 | 5/1984 | Miyamoto | 83/76 |
| 4,456,374 | 6/1984 | Langberg | 356/237 |
| 4,490,618 | 12/1984 | Cielo | 250/571 |
| 4,528,630 | 7/1985 | Sargent | 364/469 |
| 4,532,596 | 7/1985 | Pugsley | 364/469 |
| 4,603,976 | 8/1986 | Fetzer et al. | 356/402 |
| 4,608,115 | 8/1986 | Schroth et al. | 156/519 |
| 4,680,205 | 7/1987 | Lerner et al. | 428/29 |
| 4,719,575 | 1/1988 | Gnuechtel | 364/469 |
| 4,757,930 | 7/1988 | Ditto | 226/27 |
| 4,786,355 | 11/1988 | Kontz | 156/556 |
| 4,795,510 | 1/1989 | Wittrock et al. | 156/64 |
| 4,837,715 | 6/1989 | Ungpiyakul et al. | 364/552 |
| 4,955,265 | 9/1990 | Nakagawa et al. | 83/74 |
| 4,961,149 | 10/1990 | Schneider et al. | 364/469 |
| 5,026,458 | 6/1991 | Beuther | 162/198 |
| 5,045,135 | 9/1991 | Meissner et al. | 156/64 |
| 5,235,515 | 8/1993 | Ungpiyakul | 364/469 |

FOREIGN PATENT DOCUMENTS

| | | |
|---|---|---|
| 2027855 | 11/1991 | Canada. |
| 3325126C1 | 1/1985 | Fed. Rep. of Germany. |
| WO84/02190 | 6/1984 | PCT Int'l Appl. . |
| 1575140 | 9/1980 | United Kingdom. |
| 2143320B | 10/1986 | United Kingdom. |

OTHER PUBLICATIONS

Patent Abstracts of Japan, vol. 014, No. 543 (C-0783) Nov. 30, 1990 & JP-A-22 28 962 (Oji Paper Co. Ltd.) Abstract.

Machine Design. vol. 57, No. 19, Aug. 22, 1985, Cleveland, Ohio, USA, pp. 66–71, "The Move to Electronic Drive Shafts".

Primary Examiner—James C. Cannon
Attorney, Agent, or Firm—Paul Yee

[57] ABSTRACT

A distinctive apparatus and method for selectively providing predetermined segments of web material comprises a supplying mechanism for providing the web material. A first sensing mechanism detects a reference marker on the web material to generate at least one reference marker datum which is associated with a selected web segment. A separating mechanism includes a sensor mechanism for providing at least one separation datum, and divides the web material along a separation region during a production of the web segment. A phase regulating mechanism controls a relative phasing between the reference marker detected by the first sensing mechanism and the dividing by the separating mechanism. The phasing is conducted with respect to a set reference value. An assembling mechanism places the web segment onto a substrate, and a second sensing mechanism separately detects a location of the separation region relative to the reference marker to generate at least one location datum which is in correspondence with the separation datum. A location correlating mechanism generates at least one comparison datum associated with a web segment, and a data processing mechanism evaluates the comparison datum to generate an updated set reference value. A reference regulating mechanism selectively adjusts the phase regulating mechanism to incorporate the updated set reference value.

1 Claim, 28 Drawing Sheets

FIG. I

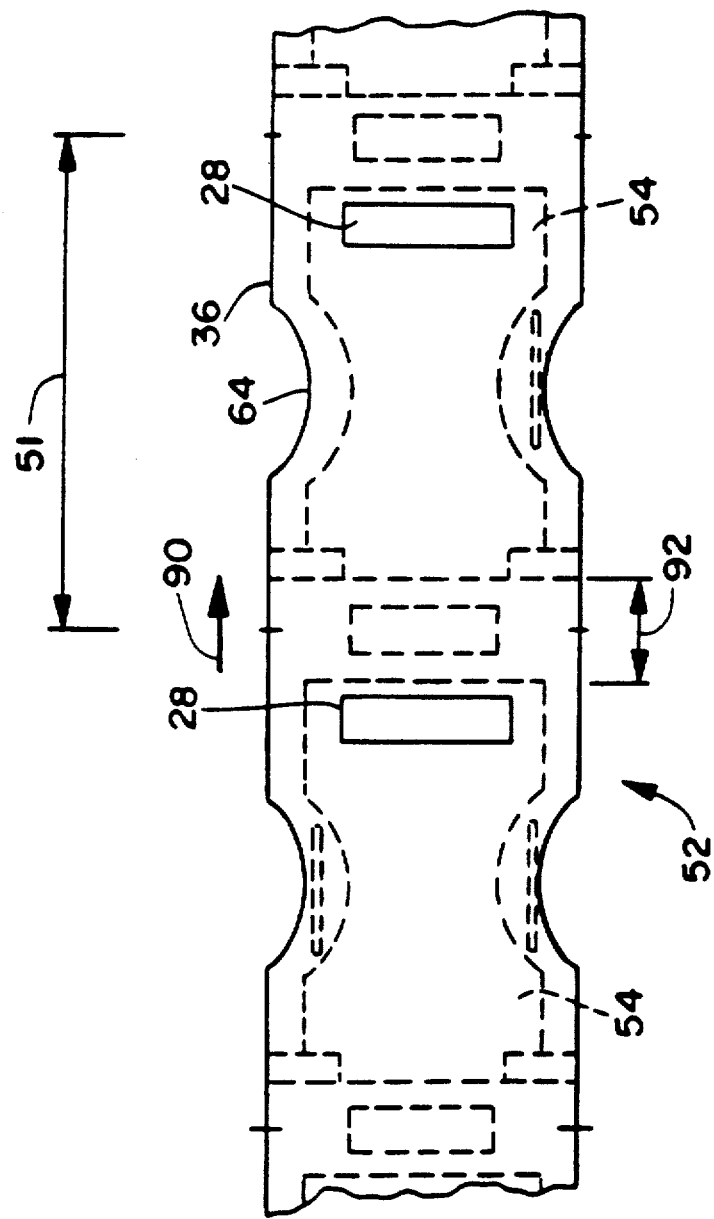

GEAR RATIO: 2.4

DIAPERS FROM SICK #1
TO KNIFE    3

SET POINT    50

SERVO ENCODER COUNTS

| 1 | 6000 |
| 2 | 12005 |
| 3 | 18002 |
| 4 | 24025 |
| 5 | 30044 |

TABLE FILLED WITH
MOTOR LOCATION
EVERY SICK #1
PULSE

CURRENT POS -
DP FROM SICK #1
= START 5-3 = 2ND POS
BEGIN SEARCH
IN POSITION 2

⇐ 30100 - KNIFE PROX

PROX LOCATION - TARGET LOCATION -
(TARGET ENCODER COUNTS TO
TRAVEL) = AMOUNT NEEDED TO
PHASE

PHASE 45
COUNTS

30100 - 12005 - (6000 * 3 + 50)
= 45 ENCODER COUNTS

WHERE 6000 = (GEAR RATIO) * (PULSES PER REVOLUTION,
= (2.4) * (2500)               ENCODER 82)

FIG. 15

| SICK #1 | CHANGE | CUMUL |
|---|---|---|
| 3990 | -10 | -10 |
| 4010 | 10 | 0 |
| 4020 | 20 | 20 |
| 4100 | 100 | 120 |
| 4200 | 200 | 320 |

- ASSUME ACCUMULATION HAD TO EXCEED 300 COUNTS BEFORE CORRECTION WAS MADE

- THEREFORE, 320 COUNTS/5 SAMPLES EQUALS A 64 COUNT PHASE VALUE

- ONCE PHASED, THE CUMULATIVE VALUE AND SAMPLE COUNTER WILL BE RESET TO ZERO

FIG. 16

A RUNNING AVERAGE OF THE SET POINTS IS
CALCULATED EVERY DIAPER. i.e. THE NEWEST
VALUE IS ADDED TO THE SUM AND THE OLDEST
IS SUBTRACTED.

THE ACTUAL BUFFER IS 32 LOCATIONS LONG

SP_SUM% = 24440
SP_AVG% = 6110

ADJUSTED SUM

24440 + 6250 - 6200
= 24490
NEW AVERAGE = 6122

- THE SET POINT IS UPDATED EVERY
SMALL_UPDATE% (4) DIAPERS AFTER
BIG_UPDATE (25) DAIPERS OF DATA IS IN
SP_BUFFER%.

- DURING A SPLICE, THE BUFFER IS CLEARED AND
THE SET POINT IS UPDATED EVERY
SMALL_UPDATE% DIAPERS FOR
APPROXIMATELY 30 DIAPERS.

FIG. 22

- COLLECT NUMBER OF ENCODER PULSES FROM MOTOR BETWEEN SICK PULSES.

- THIS NUMBER DIVIDED BY 10000 IS THE GEAR RATIO.

EXAMPLE: SICK #1 DETECTOR

| | OB | OB | OB |
|---|---|---|---|
| FEED NEEDED | | 1.80 IN | 1.75 IN |
| ENCODER PULSES | | 24700 | 24000 |
| RATIO NEEDED | | 2.47 | 2.40 |

- AVERAGE CALCULATED RATIOS OVER SAMPLE PERIOD.

- COLLECT BOTH MOTOR AND LINE SHAFT ENCODER VALUES EVERY FEW "TICKS".

- DETERMINE NUMBER OF PULSES THAT HAVE PASSED FOR EACH.

- SUM EACH OVER A SAMPLE SIZE.

EXAMPLE:  MOTOR TRAVELS 24,000 ENCODER PULSES.

LINE SHAFT TRAVELS 9,800 ENCODER PULSES.

GEAR RATIO = 24,000/9,800 = 2.45

CAN USE THIS CONCEPT TO COLLECT DATA FOR LARGER SAMPLE SIZE.

FIG. 25 ns and Placement of
METHOD AND APPARATUS FOR CONTROLLING THE CUTTING AND PLACEMENT OF COMPONENTS ON A MOVING SUBSTRATE, AND ARTICLE MADE THEREWITH This is a divisional application of copending application Ser. No. 07/832,511, filed on Feb. 7, 1992, now U.S. Pat. No. 5,235,515.

FIELD OF THE INVENTION

The present invention relates to a distinctive method and apparatus for selectively shaping and placing component elements onto a moving substrate material. More particularly, the present invention relates to a method and apparatus for cutting and placing onto a moving substrate layer a discrete patch of web material which includes an individually distinct set of graphics thereon.

BACKGROUND OF THE INVENTION

Various photo/optical techniques have been employed to inspect the quality of moving webs. For example, PCT Application WO 84/02190 by J. Kuusi, published Jun. 7, 1984, describes a procedure and means for nondestructively measuring the distribution of filler and/or coating materials in the thickness direction of paper or cardboard. Radiation from a radio-isotope source is employed to excite characteristic X-ray radiation of a component of the material.

U.S. Pat. No. 4,456,374 issued Jun. 26, 1984 to E. Langberg describes a method and apparatus for determining the presence or absence of a coating on a substrate. The technique involves placing the substrate into optical contact with a light guide and utilizing the principle of frustrated total internal reflection. Light scattered from the coating surface is monitored to indicate the presence of a coating.

U.S. Pat. No. 4,490,618 issued Dec. 25, 1984 to P. Ciello describes an apparatus for analyzing the surface of a fibrous web, such as a paper or a textile. The apparatus includes a prism structure, one surface of which is placed in contact with the fibrous web under a predetermined pressure. A collimated light beam is directed into the prism and light reflected from the contact surface through the prism is directed to a detector. The detector senses the light reflected by the contact surface as well as the light diffracted at the contact surface to indicate the surface condition of the fibrous web.

U.S. Pat. No. 4,955,265 issued Sep. 11, 1990 to H. Nakagawa et al. describes a web cutting position control system capable of cutting a web having a print pattern thereon. The system includes a counter for counting the rotational pulses of a cutting cylinder for cutting the web is provided so as to compare the pulse count at the time of synchronizing mark detection with the reference value representing a value at the moment when the web and the cutting cylinder are in normal relative positions, and to control the relative positions of the web and the cutting cylinder to the normal relative positions by controlling the movement of a compensating roller until the two values become equal to each other.

U.S. Pat. No. 4,795,510 issued Jan. 3, 1989 to M. Wittrock et al. describes a technique for assembling a reinforcement patch of material onto the outer cover material of an absorbent article. The technique employs a knife roll and a vacuum slip anvil roll.

British Patent 1,575,140 published 17 September 1980 and issued to SICK GmbH describes an electro-optical monitoring system for checking the presence of creases or other surface irregularities on a moving web of material. The monitoring apparatus directs a sharply defined light beam at a slightly skewed angle relative to a curved surface of the web. A photoelectric light detecting means detects light from the light beam to generate an output signal. The output signal changes in response to the entry of an irregularity into the light beam.

Conventional devices and techniques, such as those discussed above, have not been sufficiently effective for automatically adjusting a cutting or other separation process for producing predetermined segments of web material while keeping the parameters of the web segment within acceptance specifications. As a result, the web material may be cut at improper positions along the web length, and the resultant incorrect web segments can cause the manufactured product to be out of specification. The production line can suffer excessive downtime and reduced production efficiency.

BRIEF DESCRIPTION OF THE INVENTION

The present invention provides a distinctive method and apparatus for selectively providing predetermined segments of web material. Generally stated, the apparatus includes supplying means for providing the web material, and a first sensing means for detecting a reference mark on the web material and generating at least one reference mark datum which is associated with a selected web segment. A separating means provides at least one separation datum and divides the web material along a separation region during a production of the web segment. A phase regulating means controls a relative phasing between the reference marker detected by the first sensing means and the dividing of the web material by the separating means. The phasing is conducted with respect to a set reference value. Assembling means place the web onto a substrate, and second sensing means separately detects a location of the separation region relative to the reference mark to generate at least one location datum. A location correlating means evaluates the location datum to generate an updated set reference value, and a reference regulating means provides for a selective adjustment of the phase regulating means to incorporate the updated set reference value.

The present invention also provides a distinctive method for selectively providing predetermined segments of web material. Generally stated, the method includes the steps of supplying the web material at a web speed and sensing a reference mark on the web material to generate at least one reference mark datum which is associated with a selected web segment. A separation datum is provided and the web material is divided along a separation region during a production of the web segment. A relative phasing, between the sensing of the reference marker and the dividing of the web material, is controlled. The phase control is conducted with respect to a set reference value. The web segment is placed onto a substrate, and a location of the separation region relative to the reference mark is separately detected to generate at least one location datum. The location datum is evaluated to generate an updated set reference value, and the phase controlling step is adjusted to incorporate the updated set reference value.

A further, article aspect of the invention comprises a backsheet layer, and a substantially liquid permeable topsheet layer which is disposed in an adjacent facing relation with said backsheet layer. An absorbent pad is sandwiched between the topsheet and backsheet layers, and a relatively smaller patch of web material secured to an inward or outward facing surface of said backsheet layer. The patch has thereon a predetermined set of graphics which is congruously entire, and at least one reference marker portion. The reference marker portion is constructed to provide for a selected separating of the predetermined set of graphics from an interconnected plurality of graphic sets.

The present invention can efficiently evaluate and control a web moving at high speed to ascertain the configuration and relative positional placements of selected component elements. In particular, the invention can provide accurate, real-time information on each article during the production process, and can rapidly adjust the process line to provide a desired configuration and placement of the components. An improved article can be manufactured with enhanced quality and reduced levels of waste.

BRIEF DESCRIPTION OF THE DRAWINGS

The present invention will be more fully understood and further advantages will become apparent when reference is made to the following detailed description of the invention and the drawings, in which:

FIG. 3 representatively shows a composite web composed of an interconnected plurality of diaper articles;

FIG. 15 representatively shows a simplified example of a buffer search employed to provide for phasing adjustments;

FIG. 16 representatively shows a simplified example of a phasing adjustment generated through integral control;

FIG. 22 representatively shows an example of calculating a running average of set point values;

FIG. 25 representatively shows an example of another method for determining the gear ratio value.

DETAILED DESCRIPTION OF THE INVENTION

Figure 1:
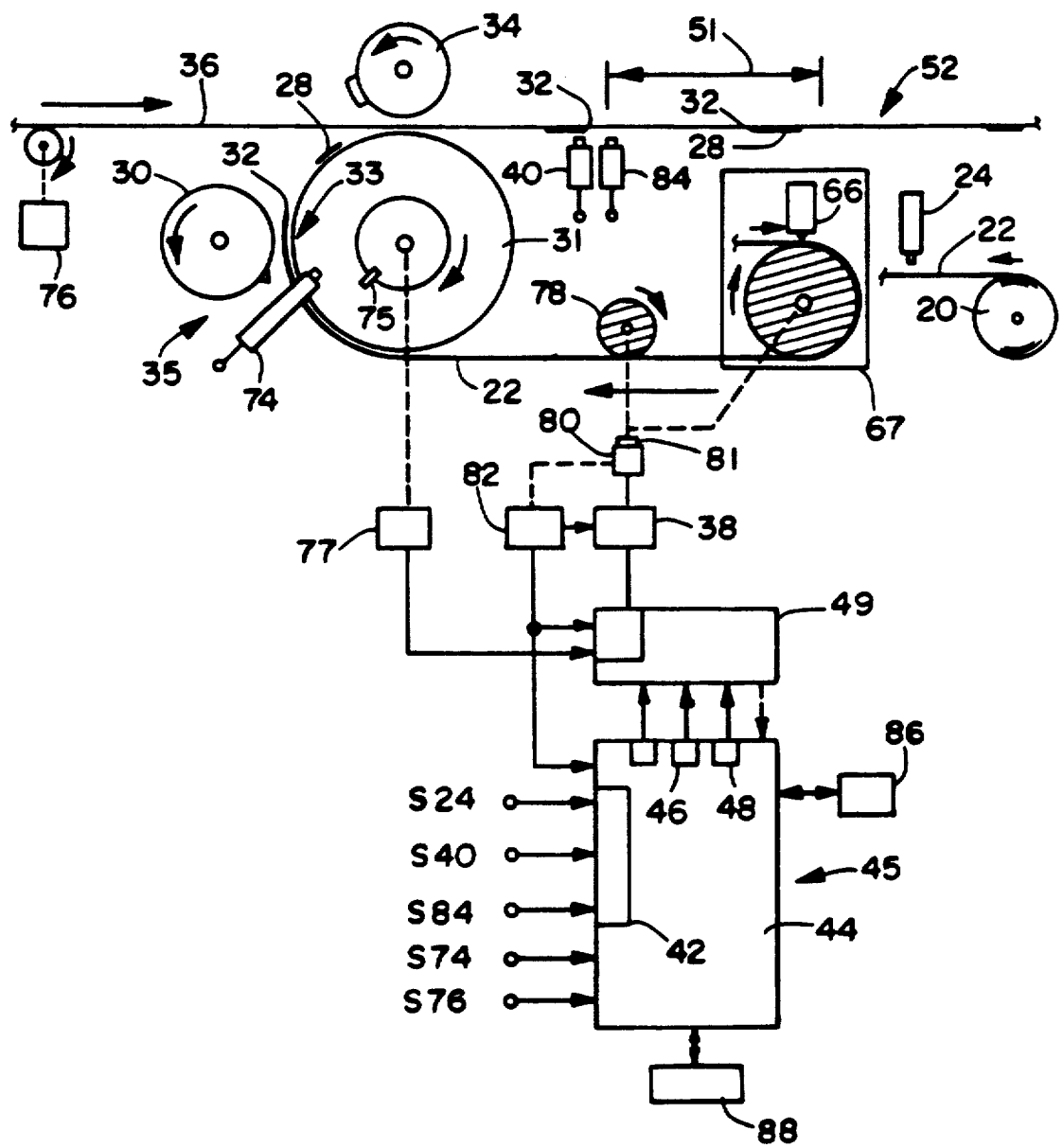
FIG. 1 shows a schematic representation of an apparatus of the invention.
Figure 2:
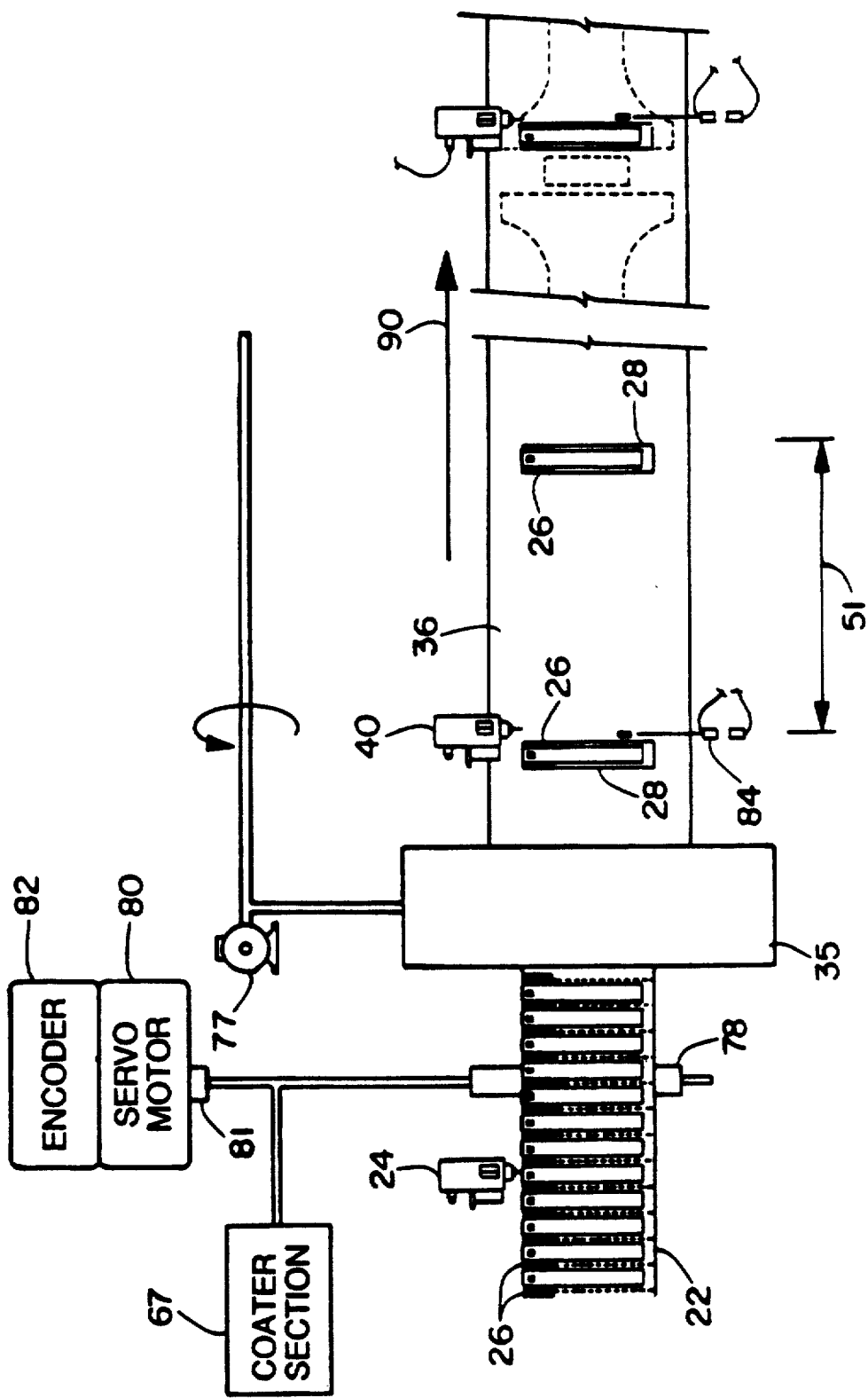
FIG. 2 shows another schematic representation of an apparatus of the invention with additional detail regarding the reference marking means on the web material.

Referring to FIG. 1, a representative apparatus of the present invention for selectively providing predetermined segments of web material includes supplying means, such as web supply roll 20 and feed roller 78, for providing web material 22. First sensing means, such as sensor 24 detects a marking means, such as reference marker 26 (FIG. 2), on web material 22 and generates at least one reference mark datum which is associated with a selected web segment 28. A separating means, such as knife roll 30 and anvil roll 31, includes indicating means, such as proximity switch 74, for generating at least one separation datum, and divides web material 22 along a separation region 32 during a production of the web segment. Assembling means, such as stomper roll 34, places web segment 28 onto a substrate 36. A phase regulating means, such as servo motor 80 with gear box 81 and a variable-speed electronic drive 38, controls an incremental, relative phasing between the reference marker detected by first sensor 24 and the dividing of web material 22 produced by the separating means at cut location 33. The incremental phasing is conducted with respect to a set reference value, such as a set point employed by a control system 49. A remotely positioned second sensing means, such as second sensor 40, separately detects a location of separation region 32 relative to its associated reference marker 26 to generate at least one location datum. Location correlating means, such as a mechanism comprising location evaluator 42 within computer 45, evaluates the location datum to generate an updated set reference value. In a particular aspect of the invention, the location correlating means generates at least one comparison datum associated with the web segment. A data processing means, such as a data processor portion 44 of computer 45 and a portion of Distributed Control System 49, evaluates the comparison datum to generate the updated set reference value. Reference regulating means, such as reference regulator 46, provides for a selective adjustment of control system 49 to incorporate the updated set reference value.

A particular aspect of the invention can also include a gear ratio control means, such as gear ratio controller section 48 of computer 45. The gear ratio controller can provide for a selective adjustment of a relative speed at which web material 22 is provided by web feed roll 78.

A data input device 88, such as an IBM-compatible personal computer (PC), is employed to allow an operator to provide the method and apparatus with any required operating parameters. An example of a suitable computer is a COMPAC III personal computer. In addition, a monitoring system 86, such as a NEMA-TRON display unit, can be employed to display operational data and system status. An example of a suitable display monitor is a NEMATRON IWS 1523 cathode ray tube (CRT) device which is available from NEMA-TRON, subsidiary of Interface Systems, Inc., a business having offices in Ann Arbor, Mich.

For the purposes of the present description, the terms "datum", "data" and "signal" are to be interpreted in a general sense, and are meant to designate various types of characterizing information produced during the operation of the invention. Such types of information can include, but are not limited to, information in the form of mechanical, magnetic, electrical or electromagnetic impulses, or combinations thereof.

The following detailed description will be made in the context of a substrate layer 36 which is a component layer employed to construct an interconnected plurality of absorbent articles, such as disposable diapers, incontinence garments, sanitary napkins, training pants, caps, gowns, drapes and the like. It should be readily apparent, however, that the method and apparatus of the present invention may also be employed with other types of substrates and other types of articles. For the purposes of the present description, the term "component" is intended to designate selected regions, such as cut edges and the like, as well as structural members, such as elastic strips and absorbent pads, which might comprise selected structure, such as web material 22, substrate 36 or a composite substrate assembly. While the following detailed description is made in the context of determining and controlling the relative placements of web segments or patches, it is readily apparent that the method and apparatus of the invention can be employed to determine and control on substrate 36 the relative locations of other components, such as elastic strips, absorbent pads, tabs, tapes, and the like.

Figure 3A:
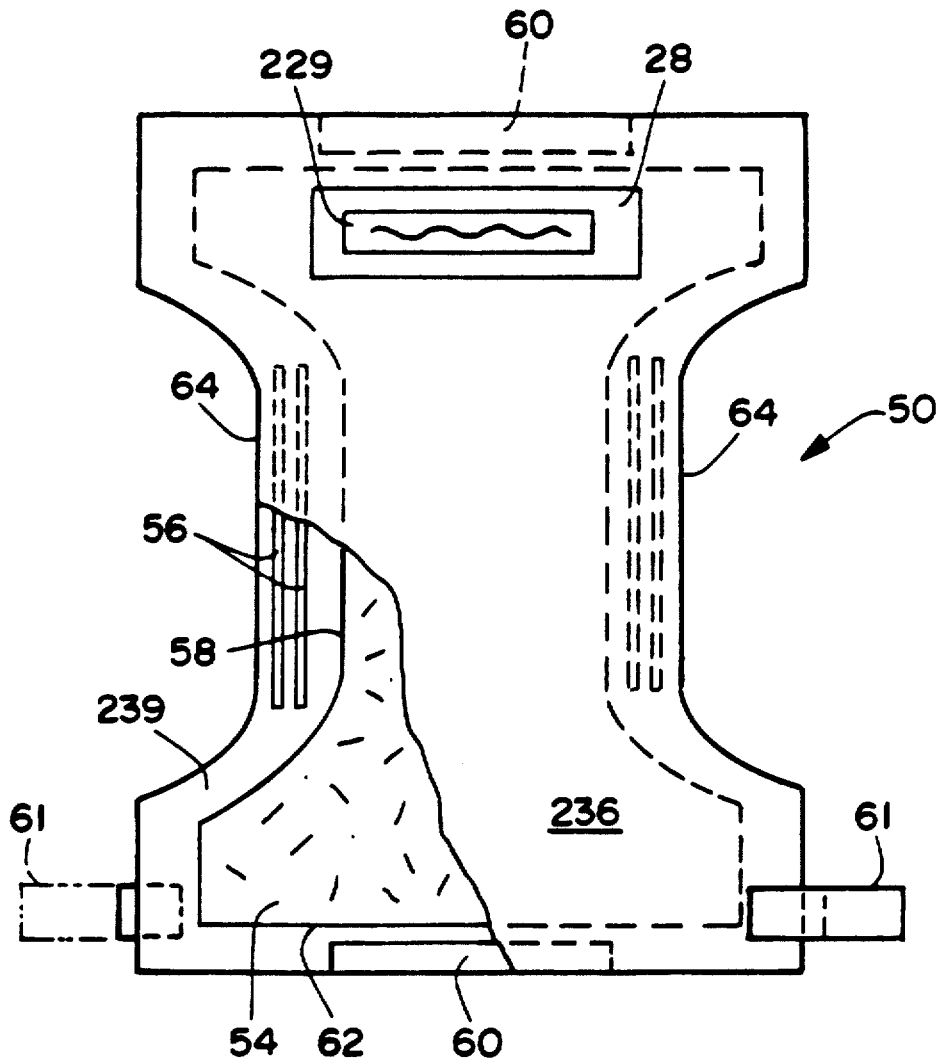
FIG. 3A representatively shows a partially cut away example of an individual diaper article of the invention.

In the embodiment representatively shown in FIG. 3, substrate 36 comprises a layer portion of composite web 52, which in turn represents an interconnected plurality of disposable diaper articles 50. For example, the illustrated embodiment of substrate 36 is a moving layer composed of a substantially liquid impermeable backsheet material, such as a polyolefin film layer. Substrate 36 may, for example, be composed of polyethylene, polypropylene, or the like. A plurality of additional components, such as absorbent pads 54 and tape-receiving patches 28, are assembled with substrate 36 to produce an interconnected plurality of diaper articles 50. The shown embodiment of composite web 52 includes pads which are substantially regularly spaced along the machine direction 90 of substrate 36. The individual, adjacent pads are separated from each other by a discrete distance 92. During the manufacturing process, the interconnected diapers are cut apart, to form individual articles, such as the diaper representatively illustrated in FIG. 3A.

With reference to FIG. 3A, a diaper article 50 is representatively shown in its fully stretched out condition with all of the elastic gathers removed. The article generally includes a backsheet layer 236, and a substantially liquid permeable topsheet layer 239 which is disposed in an adjacent facing relation with the backsheet layer. An absorbent pad 54 is sandwiched between the topsheet and backsheet layers. In the shown embodiment, the topsheet and backsheet are substantially coextensive and relatively larger than the absorbent pad. Accordingly, marginal portions of the topsheet and backsheet extend beyond the periphery of the absorbent pad to form front and rear waistband edges and lateral side edges. A relatively smaller patch of web material 228 is secured to an inward or outward facing surface of the backsheet layer. Patch 228 may, for example, provide a landing zone at the front waistband section of the diaper, and may comprise a component of a refastenable adhesive taping system. The patch is constructed and arranged to provide a suitable surface against which an adhesive fastening tape can be adhered, peeled away and re-adhered to allow for inspection and fit-adjustment of the article.

The web material employed to form the web segment patches may be any material which is consistent with the intended use of the article. For example, where the patch provides a refastenable tape landing zone, the web material is selected and constructed to be operably compatible with the adhesive tape fastening system. Suitable materials include webs composed of polyester, oriented polypropylene, unoriented polypropylene and the like. The surface of the web material may be substantially smooth, or may be selectively roughened or otherwise treated to provide desired characteristics. In a particular embodiment, the web material is a layer of unoriented polypropylene configured with a micro-embossed surface.

Preferably, the patch has thereon a predetermined set of graphics 229 which is congruously entire. The selected set of graphics on an individual diaper comprises a discrete, individually entire composition. With regard to successive diapers cut from the string of manufactured diapers, the separate compositions abruptly change from graphics set to graphics set and, therefore, from diaper to diaper because there is substantially no modulating transition between the adjacent compositions formed on the original supply roll of web material. The compositions may comprise various types graphics, such as pictorial graphics, written text, and combinations thereof. A graphic set may, for example, comprise a nursery rhyme, a song lyric, an illustration of a children's story, or a teaching aid, such as a set of numbers or a set of alphabet letters.

Backsheet 236 typically comprises a substantially liquid impermeable polymer film, such as a polyethylene film. For example, the backsheet may be a 1.25 mil thick, micro-embossed polyethylene sheet available from Edison Plastics, a business having offices located in South Plainfield, N.J., and from Consolidated Thermoplastics, -a business having offices in Schaumburg, Ill. Alternatively, the backsheet may comprise a nonwoven material which has been imparted with a desired level of liquid impermeability. In addition, the backsheet may be configured to have a selected level of gas permeability, such as permeability to water vapor, to provide a "breathable" outer cover.

Topsheet 239 is typically a nonwoven, spunbond fabric, such as a polypropylene spunbond fabric having a basis weight of about 0.7 ounce per square yard (osy) and composed of fibers of about 2.5-3 denier. Optionally, the topsheet may comprise a nonwoven fabric composed of interbonded bicomponent fibers, such as a bondedcarded web composed of polyester core, polyethylene sheath conjugate fibers. Fibers may, for example, be bonded by through-air bonding or infrared bonding to form a fabric having desired tactile and liquid handling characteristics. Suitable bicomponent fibers are available from BASF Corporation and Hoechst-Celanese Corporation. Pad 54 is typically composed of a cellulosic material, such as air laid wood pulp fluff. The pad may also comprise a coform material composed of an air laid mixture of cellulosic fibers and synthetic polymer fibers. In addition, the pad may optionally include natural or synthetic superabsorbent materials, such as pectin, carboxymethyl cellulose, guar gum, polysaccharides, cross-linked synthetic polymers and the like. For example, polymers composed of alkali metal salts of lightly cross-linked polyacrylic acid have been found to be suitable superabsorbent materials. The superabsorbent materials are available from suppliers, such as Stockhausen, Hoechst Celanese, and Dow Chemical Co. Each pad 54 can also include a tissue wrap to increase the pad's structural integrity.

It is well known that conventional diapers may further include modifications, variations and additions of particular constituent components, such as leg elastics, waist elastics, adhesive fastening tapes, mechanical fasteners, internal waste containment flaps, and/or the like. For example, with reference to FIG. 3A, leg elastic members 56 may be secured to backsheet 236 adjacent to lateral side edges 58 of each pad 54. In addition, waist elastic members 60 may be secured to the backsheet adjacent to end edges 62 of the individual pads. In conventional constructions, the various elastics are sandwiched between the backsheet and topsheet layers. Diapers which include elasticized containment flap structures are, for example, described in U.S. Pat. No. 4,704,116 entitled "Diapers with Elasticized Side Pockets" issued Nov. 3, 1987 to K. Enloe, the disclosure of which is hereby incorporated by reference to the extent that it is consistent herewith.

The various components of diaper 50 can be secured together by a number of suitable conventional techniques, such as adhesive bonding, thermal bonding or sonic bonding. Typically, extruded lines, beads or looping swirls of hot melt adhesives can be employed to secure the elastics to backsheet 236 and secure the margins of the backsheet to the corresponding margins of the topsheet layer. Such adhesives can be hot melt adhesives, pressure-sensitive adhesives, or the like. If desired, the adhesives may also be applied by conventional spray techniques or swirled filament techniques. Similarly, adhesives can be employed to bond either or both of backsheet 236 and the topsheet layer to pads 54. Preferably, side edges 64 of backsheet 236 are contoured by removing selected sections. For example, cutting means, such as a water cutter, can be employed to cut away selected edge portions corresponding to the leg openings of individual diaper articles.

Diaper 50 typically includes adhesive tape tabs 61 for securing the diaper on a wearer. To provide a refastenable taping system, the diaper can include a patch of reinforcing material, such as a web segment 28, which is secured to an inward or outward surface of the diaper backsheet. A suitable landing zone patch for a refastenable taping system is described in U.S. Pat. No. 4,753,649 entitled "Film Reinforcement for Disposable Diapers Having Refastenable Tapes" issued Jun. 28, 1988, to P. Pazdernik, the disclosure of which is hereby incorporated by reference to the extent that it is consistent herewith.

The patches of material placed upon a disposable absorbent article, such as diaper 50, have ordinarily incorporated area regions of graphics derived from supply rolls of web material having the graphics arranged in substantially continuously transitioning patterns which extended along the wound-up length of the web material. The web graphics could include repeating patterns of pictures and/or words, but no particular segment of graphics has been arranged to be a discrete, individually entire composition. Instead, the graphics at any particular section of the web material continuously transitioned into the graphics located on any preceding or succeeding section of the web material. As a result, the web material could be randomly cut or otherwise sectioned along the length of the web to produce individual web segments or patches.

Since the graphics on the web continuously transition from section to section along the web length, the particular increments of graphics created on the subsequently cut patches did not appear to be incongruous.

To promote an advantageous, developmental interaction between an infant and the caretaker, for example, it has been desirable to provide on the diaper backing sheet distinct patches which include thereon a congruently entire, predetermined set of graphics. Each set of graphics can advantageously be composed of a congruent composition of pictures, words, and combinations thereof. As representatively shown in FIG. 6, each web segment 28 has a length 96 and a width 98, and can include an entire, predetermined congruous composition such as verses, nursery rhymes, number sets, song lyrics, instructional text, or the like. Each individual set of graphics is congruously entire and complete within itself. The succeeding sets of graphics on web material 22 are spaced apart by a discrete distance, and the separate graphic sets discontinuously transition from set to set. Any two, immediately adjacent sets of graphics are substantially unrelated to each other. As a result, a generally random cutting of web material 22 into individual web segments would produce discordant sets of graphics which would be aesthetically displeasing and would provide inadequate groupings of information to an observer.

The carrying out of the present invention is particularly pertinent to the accurate formation of patch-type web segments 28 with each segment having a separately distinct, congruous set of graphics thereon. The individual web segments can be selectively divided from a continuous roll of web material 22 which includes thereon an interconnected series of the separately distinct sets of graphic. The present invention can advantageously provide for an accurately controlled cutting or other separation of web material 22 into appropriate predetermined web segments 28 each of which includes a single desired set of graphics. To provide for the proper registration and controlled cutting of web material 22, the web is provided with a reference marking means, such as a sequence of reference markers 26, as representatively shown in FIG. 6. The reference markers operatively indicate the boundaries between individual web segments 28. Preferably, the reference markers are regularly spaced at substantially equal intervals along machine direction 90 of web material 22, but alternatively, may be irregularly spaced at unequal intervals along the machine direction. In the illustrated embodiment, the reference markers are positioned adjacent a lateral side edge of web material 22 and have a width 72 which extends partially across the web width 98. Optionally, reference markers 26 may be positioned at another selected position along the cross direction 94 of web material 22, or may have a width 72 which extends completely across the width 98 of web 22. The representatively shown reference marker 26 has a discrete length dimension 70, and the reference marker extends substantially continuously along its length. In alternative embodiments, the reference marker may extend discontinuously along its length dimension, and may comprise a sequence of dots, dashes, or other machine-recognizable patterns.

Reference markers 26 can comprise any signaling mechanism which is recognizable by a machine. For example, the reference marker may comprise a physical discontinuity such as notch, a protrusion, a depression, or a hole formed in the web material. Similarly, the reference marker may comprise a region of magnetic discontinuity, electrical discontinuity, electromagnetic discontinuity, or any combination thereof. The illustrated embodiment of the invention, for example, can employ a reference marker system which operates on the basis of generating a detectable electromagnetic discontinuity. More particularly, the shown embodiment of reference marker 26 provides an optical marker which operates on the basis of providing detectable changes in the intensities of visible and/or non-visible wavelengths of light.

Reference marker 26 may be configured in any desired size or shape. In the representatively shown construction, for example, the marker may comprise a generally rectangular region which has a machine direction length dimension 70 of about 1.25 centimeters and a cross-directional width dimension 72 of about 5 centimeters. Other lengths and widths may optionally be employed. It is readily appreciated that the various detecting and sensing means employed with the present invention should be appropriately compatible with the web material and the chosen reference marker system.

Figure 6:
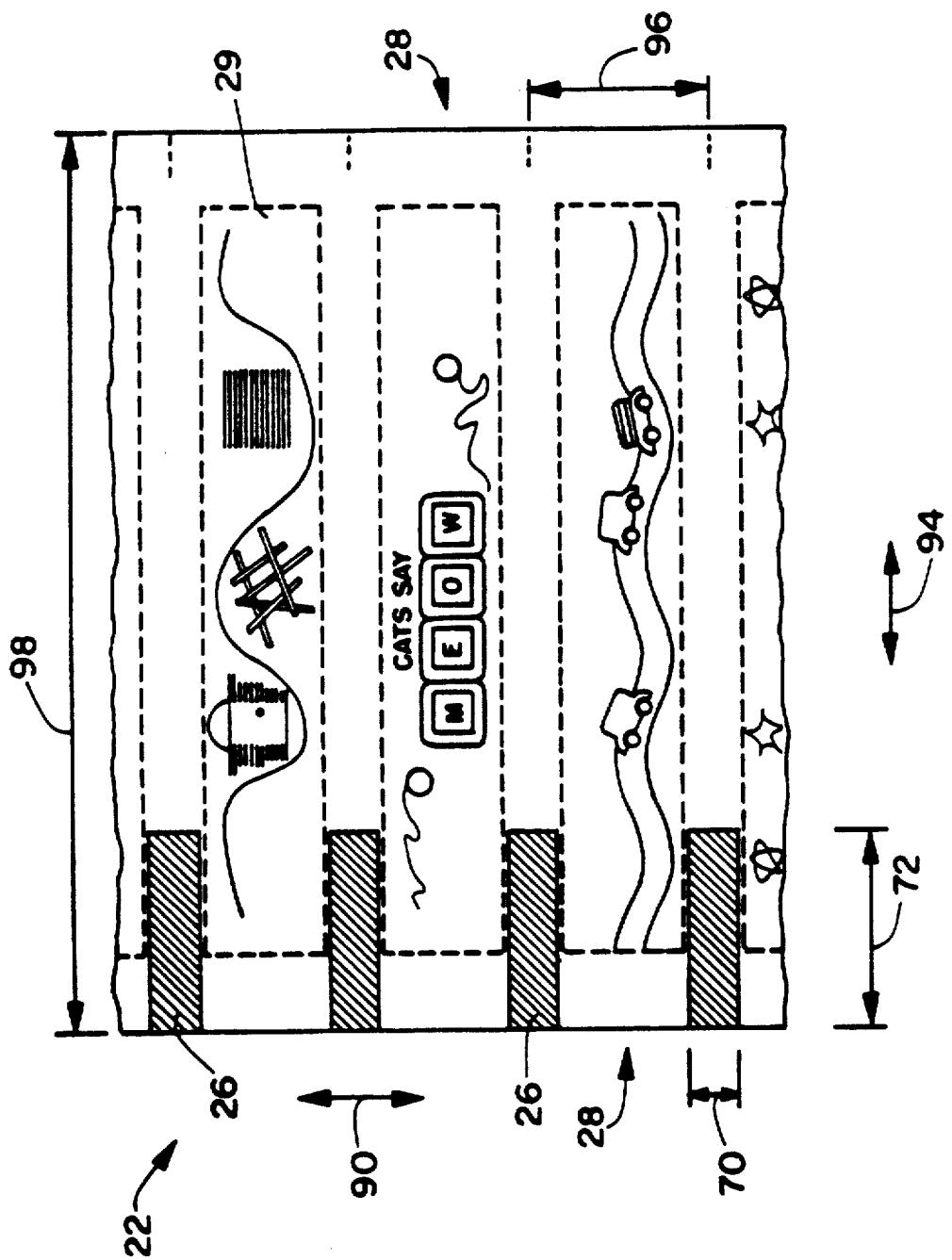
FIG. 6 representatively shows a top view of a web material which has printed thereon a series of reference markers and a series of individual, predetermined sets of graphics.

With an optical type of detecting system, the reference markers can, for example, comprise selected, discrete areas of optical brightener (OB) material which effectively define or otherwise indicate the desired boundaries of individual web segments. While the illustrated embodiment of reference markers 26 on web material 22 includes a predetermined strip of OB substance printed between two successive design patterns, as shown in FIG. 6, it should be noted that other identification marks, such as a color border detectable by a suitable color sensor, may also be used for this purpose.

In a particular aspect of the invention, the optical brightener is constructed to be sensitive to ultraviolet (UV) radiation. The optical brightener may, for example, be capable of absorbing UV radiation and then fluorescing to emit visible light spectra that can be sensed by an optical detector. UV radiation is generally understood to include electromagnetic radiation having wave lengths ranging from about 20-400 nanometers. Suitable optical brighteners include, for example, UVI-TEX OB manufactured by Ciba-Geigy, and LEUCOPURE EGM manufactured by Sandoz Chemicals Corporation. Other suitable optical brighteners include INTRA WITE OB manufactured by Crompton and Knowles, and PHORWITE K2002 manufactured by Mobay Chemical Company.

Where the reference marker system comprises markers composed of a UV sensitive optical brightener, the various sensing means and detectors can advantageously be provided by a UV activated detector, such as a SICK detector model LUT1-4 available from SICK OPTIK ELEKTRONIK, INC. a business having offices in St. Paul, Minn.

Referring to FIG. 1, a first sensor 24,-such as a UV (e.g. SICK) detector, is suitably positioned adjacent web 22 to direct UV radiation toward the moving web and to receive visible light signals generated by particular web components. In particular, as web 22 passes by sensor 24, the sensor can detect either or both edges of each reference marker 26. The two edges correspond to the leading edge and trailing edge of the reference marker as determined along the direction of movement of web 22 past first sensor 24. Sensor 24 generates corresponding electrical signals and the signals are passed to computer 45 through suitable electrical conductors S24. The desired electrical signals and associated data are appropriately stored in a buffer or other suitable storage medium within the computer.

Feed roll 78 operably moves web 22 from web supply 20 through an adhesive applicator 66 and delivers the web material to vacuum slip anvil roll 31. The adhesive applicator, disposes a suitable pattern of adhesive onto a surface of web material 22 as the web material is unwound from web supply roll 20. The adhesive pattern may be continuous or discontinuous, as desired. A suitable adhesive coating system is, for example, available from Acumeter Laboratories, a company having offices in Marlborough, Massachusetts. In the illustrated embodiment, applicator 66 comprises an adhesive coater system which is configured to dispose multiple, side-by-side strips of adhesive onto a major face surface of web material 22. For example, each individual adhesive strip can be generally continuous with a width of about 0.04-0.05 in. In addition, the adjacent adhesive strips can be spaced apart from each other along the transverse cross-direction 94 of web 22 by a distance of about 0.03-0.04 in. The adhesive operatively secures individual web segments 28 onto substrate 36 during a subsequent assembling operation. Feed roll 78 is operably driven by a servo drive motor 80, which connects to the feed roll through a suitable gear box. The servo motor can, for example, comprise a HR 2000 brushless AC servo motor available from Reliance Electric Co., a business having offices located in Cleveland, Ohio. In the illustrated embodiment, motor 80 can also be operatively coupled to drive the mechanisms within coating system 67. Drive motor 80 is operatively coupled to a drive motor encoder 82. During each revolution of drive motor encoder 82, the encoder generates a marker pulse and a selected number of phasing pulses per revolution. In the shown embodiment, encoder 82 generates 2500 phasing pulses per revolution of motor 80.

The coated web material moves to a separating means, such as a cutting mechanism composed of slip-vacuum anvil roll 31 and knife roll 30. A suitable method and apparatus for cutting and then applying web segments to a moving substrate is, for example, described in U.S. Pat. No. 4,795,510 entitled "Process for Applying Reinforcing Materials to a Diaper Cover Material" and issued Jan. 3, 1989, to M. Wittrock et al., the disclosure of which is hereby incorporated by reference to the extent that it is consistent herewith.

The representatively shown embodiment of the separating means comprises vacuum slip anvil roll 31 and knife roll 30. Anvil roll 31 provides for a vacuum which operatively holds web material 22 against the outer cylindrical periphery of the anvil roll, and is constructed and arranged to appropriately accelerate the speed of web segment 28 to match the speed of substrate 36 and thereby accommodate the proper placement of the web segment onto the substrate. Anvil roll 31 may be configured to rotate one revolution per each article length 51 of substrate 36 which passes by the anvil roll to accept a placement of a web segment 28 thereon. Alternatively, the anvil roll may be configured to deliver more than one web segment per revolution of the anvil roll. For example, anvil roll 31 may be configured to deliver two web segment patches per revolution.

The anvil roll includes a flag indicator 75 which, in the shown embodiment, is suitably mounted and geared to rotate in selected correspondence with the anvil roll. Where the anvil roll delivers one web segment patch per revolution, the flag indicator can be constructed to rotate in synchronous correspondence with the anvil roll. Where the anvil roll is constructed to deliver more than one (e.g. two) web segment patch per revolution, the flag indicator can be constructed and/or geared to rotate proportionally faster (e.g. twice as fast) to appropriately generate correct signals at the desired positional intervals.

Flag 75 is constructed and arranged to be detected by a third sensing means, such as proximity switch sensor 74. In the illustrated embodiment, flag 75 is composed of a magnetized material which can be detected by a magnetic proximity switch. Accordingly, the separating means includes an appropriate sensor which can contribute to providing a separation datum employed by the present invention. More particularly, the detection of flag 75 by proximity switch 74 can operably indicate the arrival of an individual web segment at the separating means and generate an arrival datum.

Anvil roll 31 is operatively geared to the machine line shaft to coordinate the operation of the separating means with the remainder of the manufacturing line. For example, the anvil roll can be mechanically geared to the machine line shaft. In the shown embodiment, anvil roll 31, is also operatively coupled to a reference encoder 77, which is connected to monitor and identify the operational positions of the various components in the separating means. An example of a suitable reference encoder is a BEI Motor System Company 2500 PPR Encoder, No. h25d-2500-abzc-8830-led-sm18, available from BEI Motor System Company, a business having offices in Carlsbad, Calif. Each revolution of reference encoder 77 generates a marker pulse and a selected number of phasing pulses. In the embodiment where anvil roll 31 transports two web segments per revolution, for example, reference encoder 77 is preferably configured to generate a marker pulse and 2500 phasing pulses per web segment. Accordingly, encoder 77 is configured to generate two marker pulses and 5000 phasing pulses per revolution of anvil roll 31.

The line speed at which substrate 36 moves past anvil roll 31 is typically greater than the speed at which feed roll 78 delivers web material 22 to the anvil roll. The slip vacuum aspect of anvil roll 31 provides a mechanism and technique for accelerating the movement of web segment 28 to match the movement speed of substrate 36. The peripheral speed at the outside surface of anvil roll 31 can be configured to be substantially equal to the speed of substrate 36. While web material 22 is moving slower than the peripheral speed of anvil roll 31, the vacuum applied through the peripheral surface of the anvil roll holds web material 22 against the peripheral surface while allowing a relative slipping between the web material and the peripheral surface of the anvil roll. Once the web material is cut along a separation region 32 to produce a free web segment 28, the relative slippage between the web segment and surface of the anvil roll ends, but the vacuum continues to grip the web segment against the peripheral surface of the rotating anvil roll. The rotation of the anvil roll accelerates the speed of web segment 28 to substantially match the speed of substrate 36 and place the web segment on the moving substrate. At the appropriate time, stomper roll 34 can then effectively press the web segment against the moving substrate and assemble the web segment thereto with an adhesive bond.

Knife roll 30 is operatively geared or otherwise coordinated with the rotation of anvil roll 31 to generate a web cut along separation region 32 per selected number of revolutions of the anvil roll. Alternatively, the anvil roll and knife roll can be suitably geared to generate one or more knife cuts of web 22 for each revolution of anvil roll 31. In the shown embodiment, for example, knife roll 30 is operably geared to generate two knife cuts per revolution of anvil roll 31. Similarly, stomper roll 34 is suitably geared or otherwise coordinated with anvil roll 31 to operatively press each web segment patch 28 against substrate 36 to help generate the desired attachment bond therebetween.

Figure 4A:
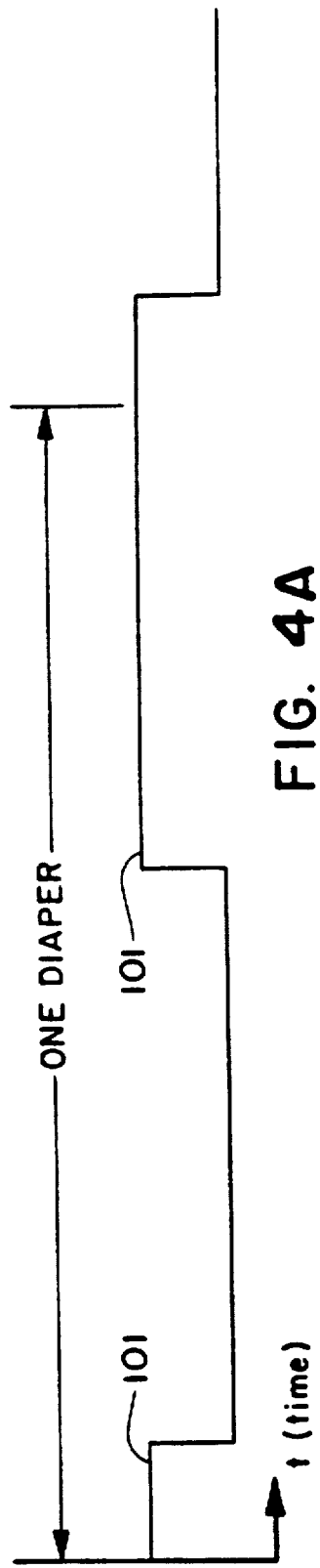
FIGS. 4A and 4B representatively show pulse signals generated by a pulse encoder.

To help accurately determine and control the location of component parts and regions of composite web 52 and its associated resultant articles, such as diaper 50, the present invention includes position indicating means, such as line shaft encoder 76. Shaft encoder 76 provides machine position reference data which can include marker pulse data corresponding to the position and presence of an individual selected article intended to be separated from composite web 52. The marker pulse data also corresponds to a particular position and phasing of the component elements relative to one another and relative to substrate 36 and composite web 52. In the shown embodiment of the invention, the marker data has the form of electrical impulse signals representatively shown in FIG. 4A. The electrical signals are routed through suitable electrical conductors S76 to a suitable processing unit, such as computer 45. In the illustrated embodiment, a marker pulse 101 occurs one time per article length 51, and is preferably configured to indicate a machine period which corresponds to a single diaper article. The marker pulse is typically employed to obtain the phase relationships between the various electrical signals and the elements of the apparatus and method. Line shaft encoder 76 is operably connected to a drive mechanism (not shown) employed to move a conveyor which transports substrate 36 through the apparatus of the invention. In addition, line shaft encoder 76 is operably connected in communication with other machine components, such as stomper roll 34, vacuum anvil roll 31 and knife roll 30. A particular arrangement may, for example, may comprise a selected, adjustable ratio gear box which can be selectively controlled to appropriately synchronize the operation of the machine components with the movement of webs, such as web material 22 and composite web 52, during the operation of the method and apparatus.

Figure 4B:
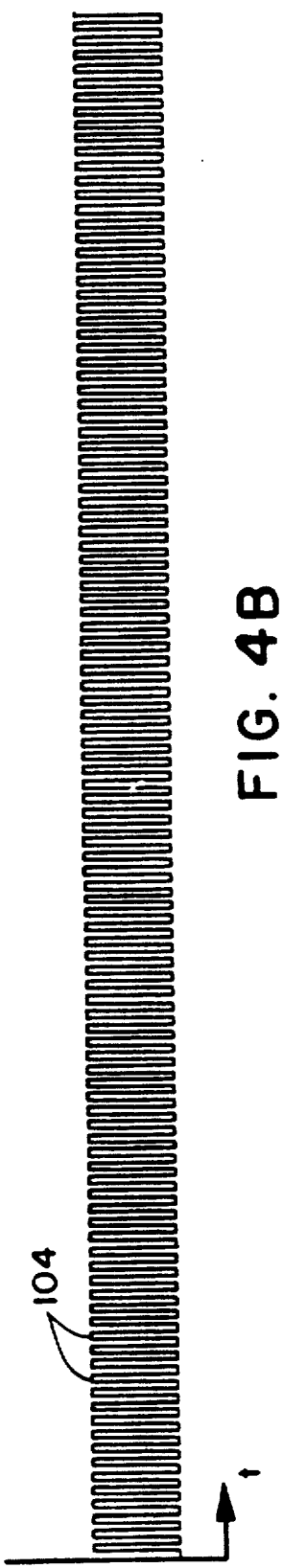
Figure 5:
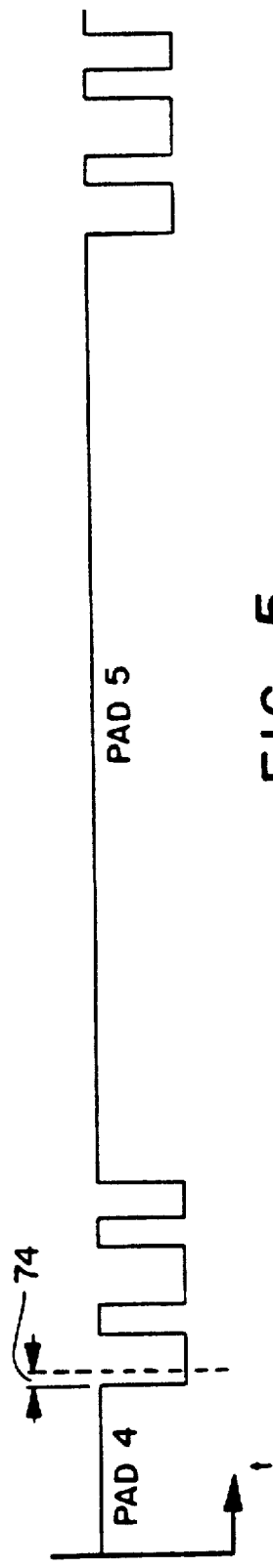
FIG. 5 representatively shows pulse signals generated by a sensor which detects the location of a cut through a reference marker.

Line shaft encoder 76 can further comprise metering means for generating substantially regularly occurring phasing pulses 104 (FIG. 4B). The line shaft encoder in the shown embodiment of the invention generates approximately 2000 phasing pulses per line shaft revolution, and thus 2000 pulses per diaper article 50. The pulses are employed as a "ruler" to measure the phase and position relationships between the various electrical signals generated by the invention, and can be employed to develop desired measurements of the distances between selected components connected to substrate 36. In the illustrated embodiment of the invention, the phasing pulses are in the form of electrical signals, which are suitably directed to computer 45 and associated control system 49 through appropriate electrical conductors S76 (FIG. 1). An example of a shaft encoder unit suitable for use with the present invention is a Model 63-P-MEF-2000-TO-OOGH90863 unit available from DYNAPAR Co., a business having offices in Gurnee, Ill.

Downstream from the cutting mechanism, a second segment sensor 40 observes the portions of reference markers 26 which remain upon each web segment 28. The shown embodiment of sensor 40 comprises a UV detector. If the separation regions 32 on a web segment 28 extend through reference markers 26, then for each web segment, sensor 40 can detect four edges from the cut-through reference markers. If any of the separation regions 32 misses passing through a reference marker 26, there can be less than four reference marker edges available for detection by sensor 40. For example, if both of the separation regions on a web segment 28 misses passing through a reference marker, sensor 40 may detect only two reference marker edges on the web segment. Data which correspond to the detected reference marker edges can provide one or more location data which are in correspondence with a particular, previously generated separation datum. In the shown embodiment, the location data are converted to electrical signals which are delivered to computer 45 through appropriate electrical conductors S40.

An optional fourth sensing means, such as sensor 84, may be employed to provide additional information regarding the presence of web segment 28 on substrate 36. For example, sensor 84 may comprise an infrared fiber optic sensor, such as a BANNER 4-6 One-Shot Amplifier with SM 53E FOW/30 Emitter and SM 53R FOW/30 Sensor, available from Banner Engineering Corp., a business having offices in Minneapolis, Minn. Sensor 84 looks for the edge of web segment 28 and operates independently from the presence of reference markers 26. The information from sensor 84 can be advantageously employed to increase the speed at which the method and apparatus of the invention can correct for misplacements of the separation regions 32. In particular, the signal data from sensor 84 can be employed to more rapidly determine and correct for situations wherein a separation region has missed passing through a reference marker 26.

In the various embodiments of the invention, particular operational components of the invention are described as being operably geared together. It should be understood that such gearing may be produced by mechanical gearing, electrical gearing, or combinations thereof. The term "gearing" generally refers to a configuration which can operably generate and maintain a desired speed relationship between selected apparatus components or process steps.

As previously mentioned, the adjacent sets of graphics on web 22 may be sufficiently unrelated such that a portion of one set of graphics would be incongruous with a portion of an adjacent set of graphics. As a result, the manufacturing process must be able to accurately cut web material 22, and a registration control system is required to control the cutting of the web material into individual segments such that each patch area contains exactly one complete set of graphics.

If the unwind and feed mechanisms, such as feed roller 78, are configured to release approximately one web segment per article length 51 of substrate movement, one could adjust the registration of the separation region 32 by varying the speed of the unwind/feed process. For example, a Reliance HR 2000 variable speed electronic drive, or a gear box with a phase correction shaft driven by a correction motor could be employed.

In conventional techniques, a "shift-register" scheme could be employed for matching detector information to a particular manufacturing operation, such as the operation of a cutter. Conventional techniques similar to those described above, may be satisfactory in a manufacturing process that does not have severe process disturbances. Examples of severe disturbances include start-ups, splices within various web materials, and non-uniform stretching of web material caused by a non-uniform winding of the web material onto the associated supply roll of material. Such disturbances can cause an improper placement of a significant number of patches and thereby increase cost and waste.

Conventional techniques have also been sensitive to the distance between the sensing means for detecting the reference marker and the cutting mechanism. The reference marker sensor has had to be placed relatively close to the cutting mechanism. If a detector is mounted a relatively large distance, such as 25 web segment lengths before the cutting unit, the phasing mechanism can phase 25 patches too soon. Where a new roll of material is spliced onto an expiring roll with the sets of patch graphics on the new roll being "out of phase" from the previous roll, up to 25 patches may be cut incorrectly. Furthermore, the individual sets of print design graphics may not be exactly equally spaced, and the relative position of the patch graphics measured at the detector may not accurately represent the relative position of the patch graphics when the web material reaches the cutting mechanism. The greater the distance between the detector and the cutting mechanism, the larger the errors can be.

In the illustrated embodiment of the invention, for example, process and mechanical constraints can make it difficult to mount a reference marker sensor close to the cutter mechanism. In particular, the coater system applies an adhesive to the reinforcement substrate to attach the patch to the diaper. Due to the presence of the adhesive, the coated side of web 22 is preferably not allowed to touch the feed roll. The reference markers 26 are on the printed side of web 22, which is also the side coated with the adhesive. The presence of the feed roll mechanism can limit accessibility to the web. Furthermore, a sensor in the vicinity of the adhesive applicator can be susceptible to adhesive contamination. As a result, a viable location of sensor 24 can be a relatively large distance of approximately 25 web segment (patch) lengths away from cut location 33.

To help illustrate the problem caused by variations in the size of the predetermined set of graphics and the distance between reference markers, one can consider a situation in which the distance between the sensor 24 and cut location 33 is about 24.5 inch (14 patch lengths) and the web segment length is about 1.75 inch per predetermined patch length 96. If the control system can hold the position of the reference marker at sensor 24 to a correct set point value, adequate registration of the desired web segment with the cut location may be achieved. A version of such a set point value is described in detail hereinbelow, and can be directly correlated to the set reference value employed by the present invention.

In practice, however, the size of the predetermined set of graphics and the distance between reference markers can vary within a roll and among rolls. For example, the predetemined patch size could increase from 1.75 inch to about 1.76 inch. Even if the control system holds the patch at sensor 24 to the exact preselected position, the actual registration could still be off by 0.14 inch (0.01 in × 14). Conventional registration control systems, however, have not adequately compensated for such a situation.

The method and apparatus of the present invention, however, can better accommodate relatively large process disturbances and can adequately control the cutting registration of predetermined web segments even when the monitoring and control sensors are place a relatively large distance from the location of the cutting operation. The present invention can also provide improved control even when the size of the predetermined set of graphics and the distance between reference markers varies in a regular or irregular pattern.

The present invention can be configured to employ a substantially uniform, predetermined registration reference marker 26 (FIG. 6) on the web material to separate one web segment patch from another. In the shown embodiment, for example, the reference marker can comprise a discrete area region of optical brightener (OB) material. A servo motor with phasing capability is electronically geared to the diaper machine to feed the web material to the cutter unit. The gear ratio of this unit, relative to the line speed of the diaper machine, may be frequently changed while the machine is running.

The sensor detecting the OB mark on the substrate web is used in conjunction with other sensors in a registration control loop that holds the position of the patch at the knife to a fixed position specified by a set point. This feature substantially ensures that precisely one patch length per diaper length is fed to the cutter unit.

The sensor detecting the OB mark on the substrate patch (after the cut) is used to calculate a "set point error". This value is then used to adjust the set point of the registration control loop. This design ensures that the registration control loop maintains a correct set point.

The desired gear ratio is calculated and updated quickly so that the web material feed rate is as close as possible to one patch length per diaper length. This feature not only compensates for any variability in the spacing between reference markers but also eliminates the need for manual gear ratio setting. Important advantages of this design are that it is fully automatic and requires only limited inputs from an operator.

Figure 7:
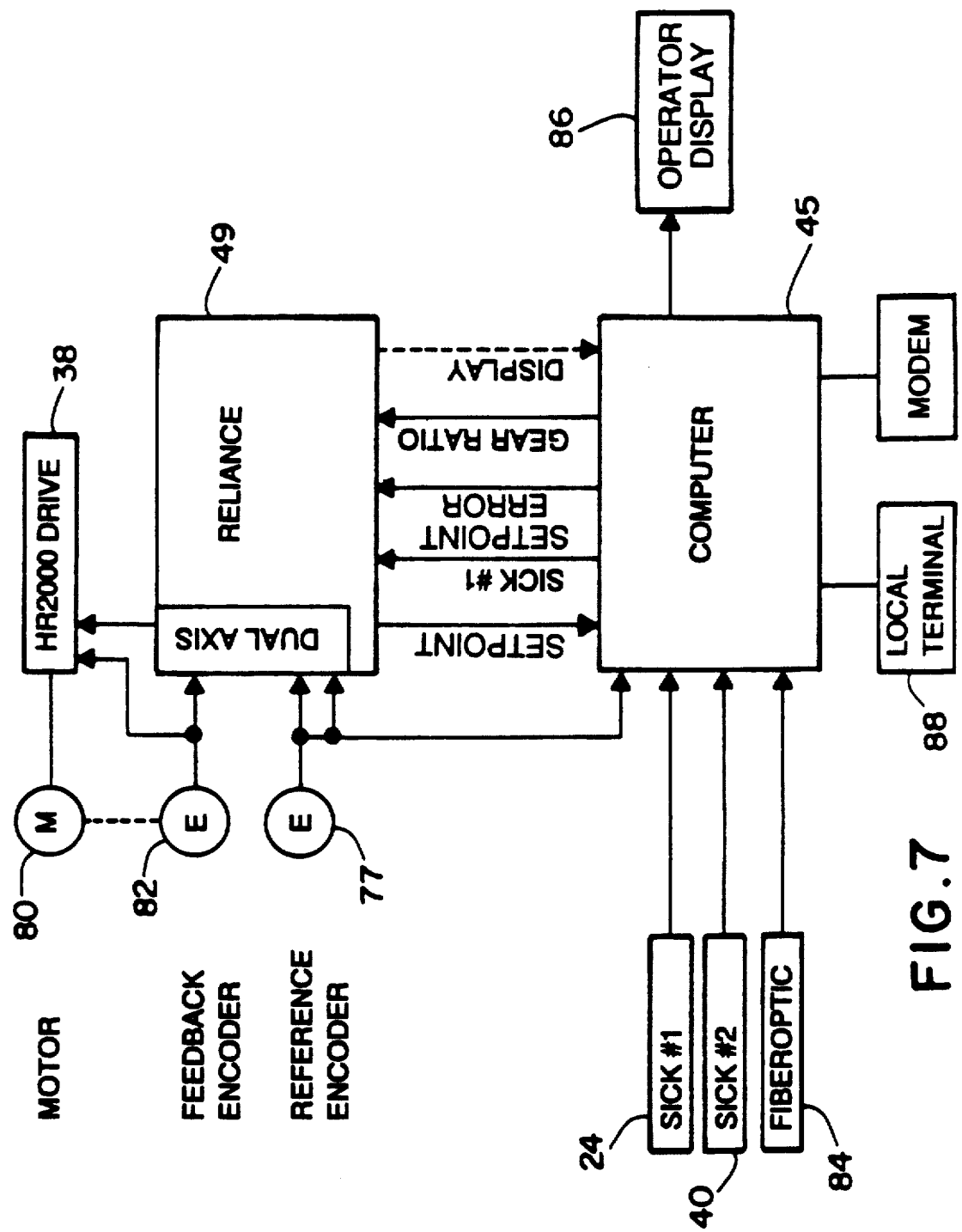
FIG. 7 representatively shows a schematic block diagram of the flow of data signals employed by the technique of the present invention.
Figure 8:
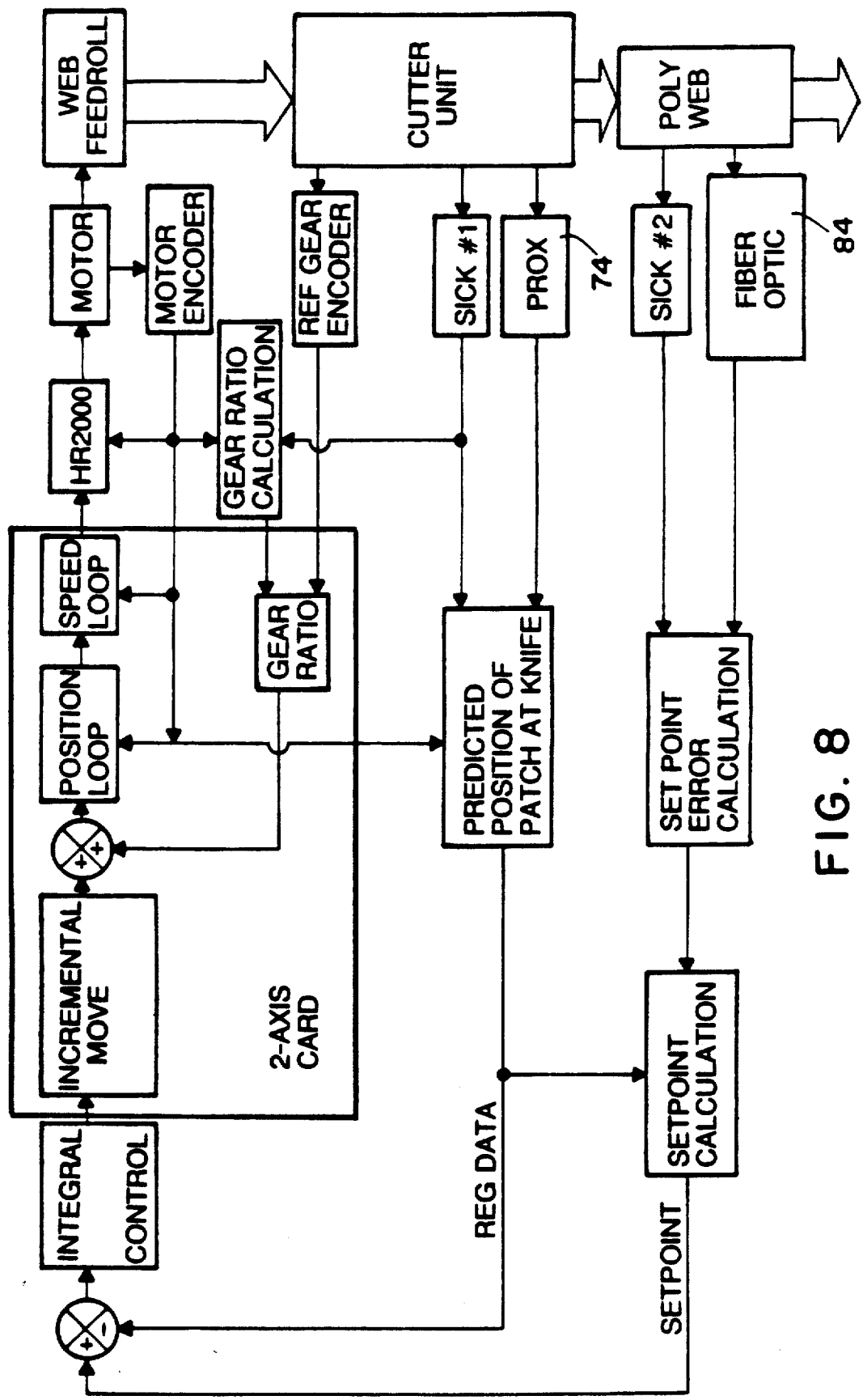
FIG. 8 representatively shows a block diagram of the control scheme employed by the present invention.

The basic control scheme for the shown embodiment of the invention is schematically set forth in FIGS. 7 and 8. FIG. 8 schematically shows a diagram of how the control structure fits together. On the right-hand side of the diagram, there is a representation of the web material 22 going through cutter unit 35 and then onto substrate material 36. The method and apparatus of the present invention controls the amount of web material sent into the cutter unit to be cut off. Since the anvil roll in the cutter unit has slip vacuum, the anvil roll will pull all of the web material that motor 80 has allowed to pass under the knife.

The phase regulating means of the present invention includes registration control means for selectively providing an incremental movement of said web material relative to the separating means to register the separation region relative to the reference marker. Generally stated, web material feed roller 78 is driven by a servo motor 80 which is in turn connected to a registration control means, such as a variable-speed electronic drive mechanism. The electronic drive can, for example, comprise a HR2000 motor drive controller regulated by an electronic control system 49, such as a Reliance Distributed Control System (DCS) made by Reliance Electric Co. The DCS system includes a Reliance Electric Automax processor and associated hardware. Since it is electrically geared to the line shaft using encoder 77 mounted on the cutter unit (e.g. on anvil roll 31), the DCS unit can change the reference marker position relative to the operation of cutter unit 35 while the production machine is running (phasing capability). The DCS can also change the gear ratio of the system while the production machine is running.

A first sensor 24, such as a first UV detector (SICK #1), is mounted as close as possible but prior to, the cutting mechanism. The signal from sensor 24 is used by a processing sequence and control loop which regulates an incremental phasing movement to keep the registration mark at substantially a constant position relative to the cutting mechanism.

The signal from sensor 24 is also employed by a gear ratio processing system to calculate a value which represents a particular amount of movement needed to unwind one patch length 96 per article length 51. This value can be converted to a gear ratio which, for example, can be employed to regulate the movement of feed roll 78 relative to the movement of the machine line shaft.

The reference markers are also detected by a second sensor 40, which may comprise a second UV detector (SICK #2). The signal data from sensor 40 can be used to calculate a set point of the incremental phasing control loop mentioned above. The signal from sensor 40 can also be used to determine whether the configuration of the web segment patch is within product specifications.

In the illustrated embodiment, sensor 24 detects the OB reference marks on web material 22 to provide reference data, and sensor 40 detects the OB marks on the web segment patches to provide location data. Another detector, such as a fiber optic (FO) infrared sensor 84, can be mounted adjacent to sensor 40. Sensor 84 can detect the edge of each web segment 28 to optionally generate additional location data. A fourth sensor is proximity switch 74, which is mounted on the cutter unit to indicate the position of the cut and provide separation data.

With reference to FIGS. 7 and 8, the four signals from sensor 24, sensor 40, infrared sensor 84 and proximity switch 74, along with the signal from drive motor encoder 82, are routed and connected to computer 45 for measurement and filtering. The computer can, for example, comprise a VME-based microprocessor. In the representatively shown embodiment, the VME unit comprises a PME 68-23 CPU which is available from Radstone Technology Corp., a business having offices in Montvale, N.J.

With respect to each diaper, VME computer 45 is configured to estimate three major variables. The variables are:

(a) A predicted position of the predetermined web segment patch 28 at the cutter unit. In the illustrated embodiment, this is the predicted arrival and centering of a particular reference marker 26 at cut location 33.

(b) A measurement which indicates how close the location of the actual separation region has come to the desired location (target) of the separation region. In the shown embodiment, this is a measurement of how close each separation region has come to bisecting an OB reference marker. This variable is called "set point error", as it is subsequently employed to update the set point value and adjust the incremental phasing sequence.

(c) A gear ratio required to suitably operate feed roll 78 to deliver to cutter unit 35 one web segment patch length 96 per diaper length 51.

The three variables calculated by VME system 45 are sent to DCS system 49, which performs the following:

(a) If the predicted position of the web material at the knife differs from the set point, the web position is adjusted by momentarily speeding up or slowing down the feed roller. This action is called "phasing" or "incremental move". This comprises the "registration control loop".

(b) The optimal gear ratio for running coater section 35 (and feed roller 78) is estimated. The optimal gear ratio is a gear ratio in which the web material is fed through the cutter unit at a rate of one patch length 96 per diaper length 51. A suitable estimation technique is an average of the filtered gear ratio measurement received from the VME system. The servo motor 80 is then commanded to follow the cutter at this gear ratio. This is the "gear ratio update processing sequence".

The "set point error" and the predicted position of the substrate at the knife (registration data) are used to estimate and update a new set point for the registration control loop. This processing sequence is called "automatic set point generation", and comprises the following technique:

(a) The set point error data is run through a filtering processing sequence to ensure that the measurement is valid.

(b) The predicted position of the substrate at the knife corresponding the same patch as the set point error is also run through a filtering processing sequence to ensure validity.

(c) If both data in (a) and (b) are valid, a "running average" of the sum of the two are used to estimate a new registration loop set point.

PREDICTED POSITION

To predict the position of the web segment position at the cutter, the following two conditions should generally apply:

(a) the variability of the tension (therefore elongation) of the web segment 22 from sensor 24 to cut location 33 is negligible, and (b) the slippage at feed roll 78 is negligible.

It is important to note that the above two conditions are not absolute and may be violated to a certain degree. The automatic set point generation feature of the invention can advantageously compensate for some effects caused by tension variability and slippage of the web material.

On the basis of the above two conditions, the position of a predetermined set of print graphics can be accurately determined by the position of the encoder 82 connecting to the motor 80 which drives feed roll 78. Regardless of the size of the web segment or the size of the individual predetermined set of print graphics, the distance between sensor 24 and cut location 33 will be substantially constant. Even though the individual distance between successive OB reference markers 26 might change from time to time, a given point on the OB mark will still travel a substantially constant, fixed number of encoder counts to reach the cut location 33 from sensor 24. A selected, given point on the OB mark (and consequently, a given point on the printed web segment) can, for example, be an edge of the OB mark. The structural configuration of having a constant number of encoder counts (constant distance) between sensor 24 and cut location 33 can be used to predict the position of the web segment print, particularly the position of the OB mark, when the web segment arrives at the cut location.

A conventional technique of handling the delay created by a relatively large separation distance between sensor 24 and cut location 33 is through the use of a "shift register". If, for example, there are 14 patch lengths from the sensor to the cutter unit, then the data measured at the sensor are put into a shift register which has a register length of 14. The output of the shift register can then be employed to represent the patch at the cutter, and there are several processing sequences that may typically be used to compensate for the movement of the patch between the detector and the knife.

The conventional shift register technique, however, has not been adequate because it can be susceptible to faulty signals. For example, if "noise" (spurious electrical signal) in the sensor output is not filtered out, the noise may erroneously be put in the shift register. The output of the shift register, therefore, will be off by one or more units. Similarly, if the sensor fails to pick up a real OB mark, then the output of the shift register will also be incorrect. Note that one single erroneous data causes all the data in the shift register to be incorrectly shifted. This is an undesirable characteristic of the shift register technique.

Figure 9:
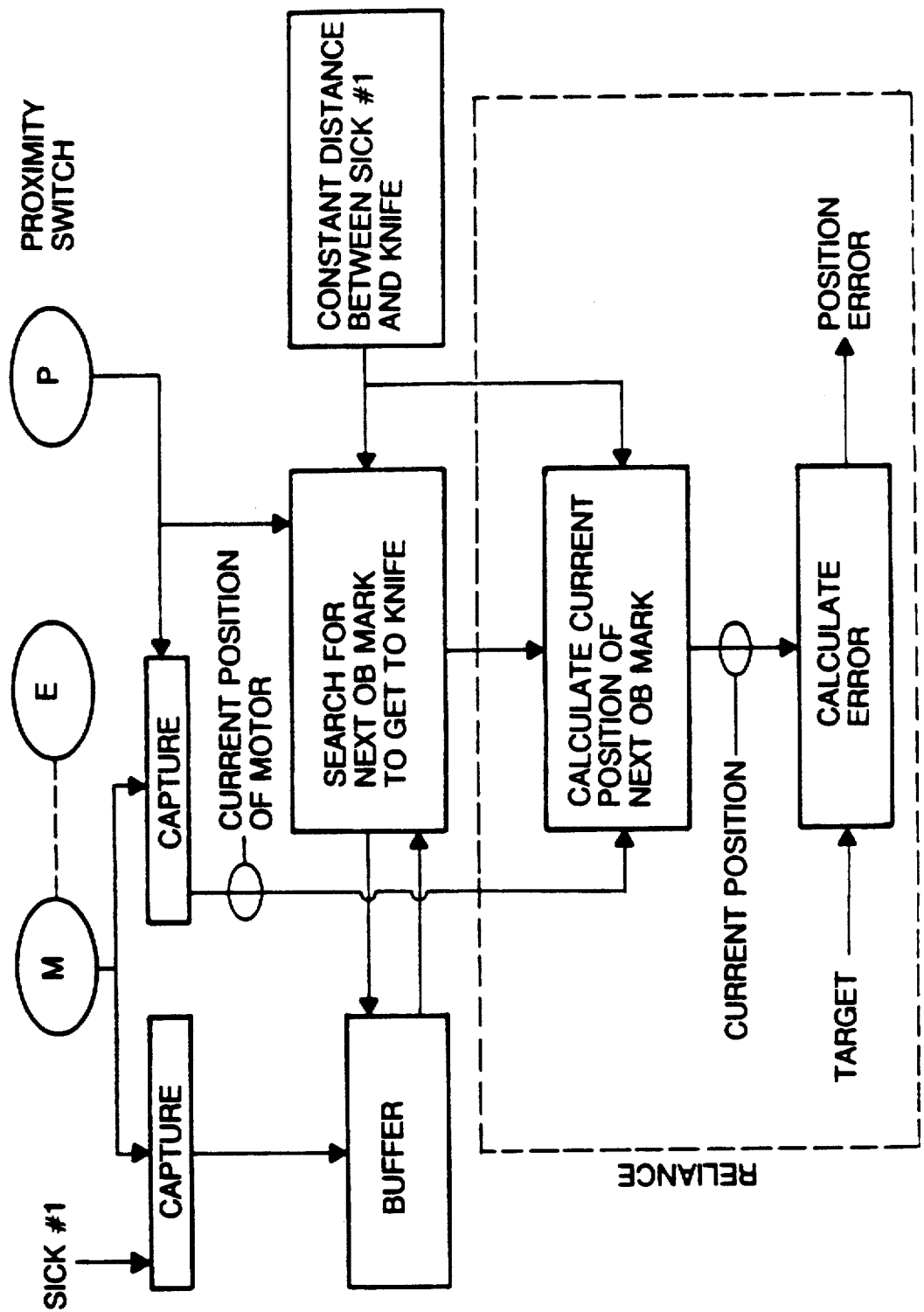
FIG. 9 representatively shows a block diagram of the tracking technique employed in pitch-distance, phase adjustment mechanism of the invention.

To minimize the effects of erroneous measurement, the present invention advantageously employs the "tracking" method schematically shown in FIG. 9. In the illustrated configuration, it is assumed that the total range of variability of web segment patch length 96 does not exceed 50% of one patch length. For example, if the nominal spacing between the sensor and the cutter is 14 patch lengths, then it is assumed that the print design spacing (distance between OB marks) will not change severely enough to place less than 13.5 nor more than 14.5 patches between the sensor and the cutter. It should be pointed out that it is not catastrophic if this condition is violated; only a slight degradation in performance will occur.

The shown embodiment of the tracking method employs the "fixed distance between the sensor and the cutter" as a reference. The main concept behind this type of control is that there is a constant physical distance between sensor 24 and the cutting location. This means that the motor encoder has to count a constant amount of pulses for an OB mark to travel from sensor 24 to the knife. In the shown embodiment of the invention, the fixed distance reference is divided into two parts. The first part is a generally constant (but selectable) unit value, measured in encoder counts. This constant unit value can, for example, be selected to generally specify the integral number of whole patch lengths that are to be located within the distance between the sensor 24 and the cutter. The number of patch lengths can be suitably expressed in terms of encoder counts and can be referred to as the tracking "target". The second part is a remainder unit value, measured in encoder counts, representing the partial patch length, if any, that is to be located within the distance between the sensor and the cutter. This second number is referred to as the "set point" of the registration control loop mentioned earlier. It is readily apparent that the set point value is directly related to the set reference value, and any change of the set point produces a corresponding change in the set reference value.

A particular configuration of the invention, for example, can have a "target" of 18,000 encoder counts and a "set point" of 50 counts. In such an arrangement, the 18,000 counts could represent three patches with 6000 counts per patch length of 1.75 inches. The distance between sensor 24 and cut location 33 would correspond to 18,050 encoder counts.

In a particular aspect of the invention, each predetermined web segment 28 can be identified by a particular OB marker. The illustrated embodiment, for example, has each web segment identified by an OB marker positioned at the leading edge of the web segment. Since each encoder count represents a discrete unit of movement, the position of each identified web segment can be tracked by detemining the number of encoder counts that have occurred since the time that the web segment and its OB marker have passed by a specific, predetermined point. For example, once an OB marker passes by the point of sensor 24, the subsequent location of the OB marker (and its associated web segment) along the direction of movement of web material 22 can be determined by tracking the number of encoder counts that occur after the OB marker has passed sensor 24.

For a selected sensor output, such as each falling edge of the signal from sensor 24 caused by the passage of an OB marker, the computer of the illustrated embodiment of the invention calculates the number of counts that went by since the last signal from the sensor. In addition, a computer routine captures a position of motor encoder 82 in terms of a number value, filters the number, and stores it in a circular buffer. The shown embodiment of the invention, for example, employs within computer 45 a counter which decrements by one count each time an encoder pulse is received from motor encoder 82. The counter decrements from approximately 16,000,000 down to zero, and is reset when it hits zero. The counter generates data, such as number values, which correspond to relative position. Each number value in the circular buffer corresponds to an OB marker (web segment) seen by sensor 24, and the numbers stored in the buffer are used every time a proximity signal is received from proximity switch 74.

When the signal from proximity switch 74 mounted on the cutter unit is received, a second computer routine captures the position of motor encoder 82. This routine then searches the circular buffer for a value representing the particular patch that is arriving at the cutter. To do the search, a "set reference" is calculated by adding the "target" and the "set point" values. The search routine then calculates the relative difference between; (a) a number value representing the proximity switch position, and (b) a number value representing the position of a patch stored in the buffer. If this calculated number value is within the number of encoder counts corresponding to the "set reference", plus or minus ½ patch length, then the entry of the buffer is taken to represent the patch that has travelled from sensor 24 and is just arriving at the cutter. Although not necessary, this procedure is preferably repeated to search the entire buffer to ensure that the best candidate number value is found.

Thus, by using the known number of encoder counts (distance) between sensor 24 and the cutting location at the cutter unit, the computer can find a value which corresponds to the OB marker (and corresponding web segment patch) which is arriving at the cutter. From this value, the computer can calculate the number of motor encoder counts that passed to get the patch to the machine position identified by the signal from the proximity switch. This number is compared to the "set reference", and the difference provides for one or more phasing error data, such as registration error signals, which are sent to the Reliance Distributed Control System (DCS) 49. The registration error signal is employed to advance or retard the movement of motor 80 (and web material 22), such as by using integral-type control. Alternatively, proportional control, or a combination of integral and proportional control may be employed.

Accordingly, the registration control means of the invention can provide a registration correlating means for matching the reference marker datum to the separation datum to generate at least one phasing datum. The phasing datum is compared with the set reference to generate a phasing error datum which is employed to determine an amount of said incremental movement of web material.

Set Point Error Measurement and Set Point Update

The set point is calculated from data provided by sensors 40 and 84 after the cutter unit, and from registration data coming out of the circular buffer derived from sensor 24. Sensors 40 and 84 look at the cut web segments, and data from these sensors can be used to determine whether the current set point is accurate (set point error). If it is not accurate, the set point can be automatically updated.

FIG. 6 shows the appearance of the OB mark on the web material. After the web material is cut into individual patches, the OB mark on an individual web segment may resemble those in FIGS. 10 or 11. Since the gear ratio update processing sequence of the invention substantially ensures that approximately one patch is unwound per cut, the probability of cutting a patch without including some portion of an OB mark is extremely small.

Figure 10:
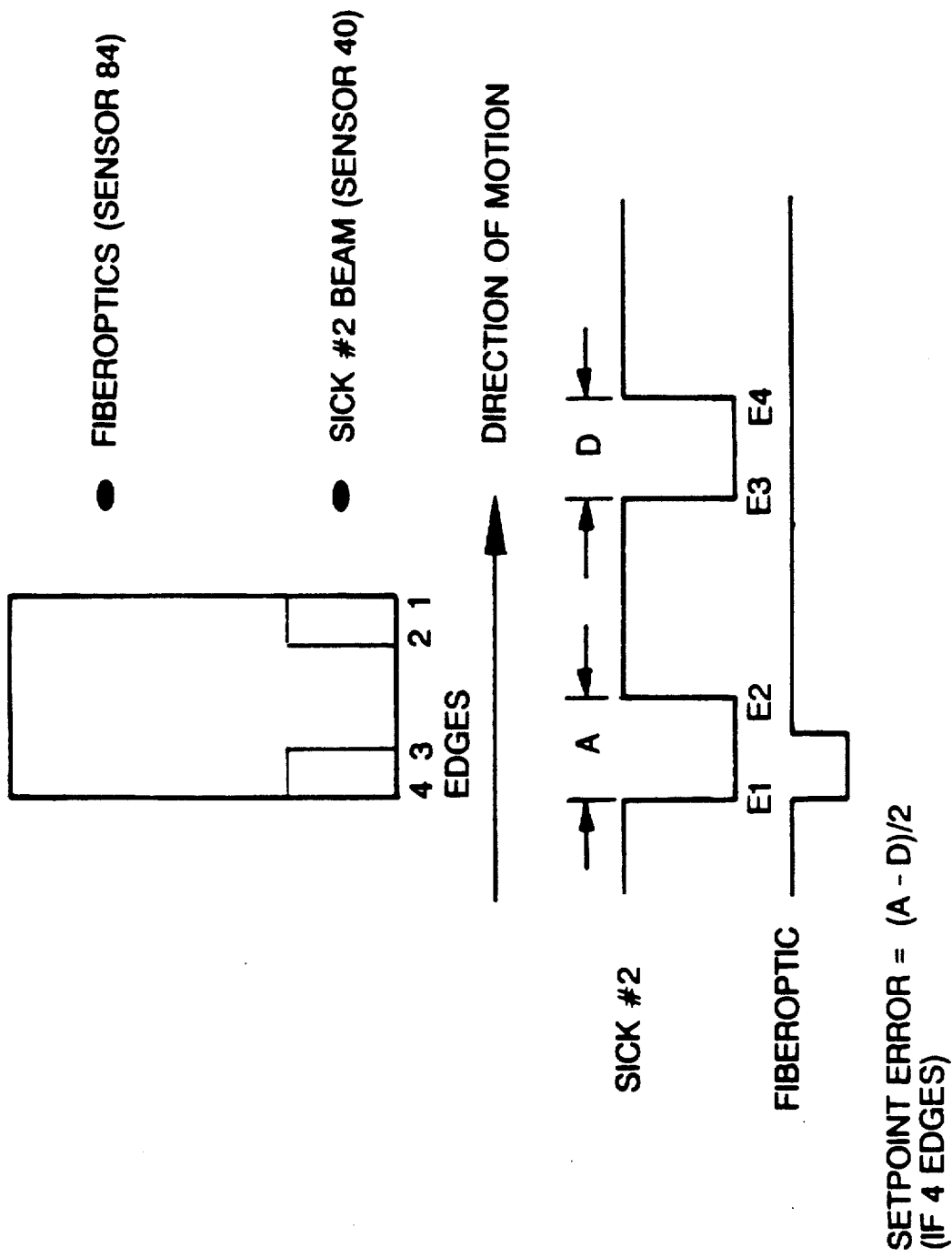
FIG. 10 representatively shows a web segment patch with two reference marker portions thereon, and representatively shows corresponding signal pulses generated in response thereto.

If the registration control loop has a set point sufficiently close to the correct value, an OB mark will be cut into two individual portions, and if the web material cutting process is at ideal registration, the OB mark will be cut into two equal portions (FIG. 10). The portion of OB mark on the right side of FIG. 10 is from one OB mark. When this OB portion (area) travels past the UV detector, the signal representing this OB area provides a location datum which is illustrated by the width "A". The OB area on the left side of the patch in FIG. 10 is from the following OB mark. The signal representing this area is labeled "D" and provides a second location datum.

If the cutting process is in registration, then distance "A" and "D" would be equal. Accordingly, an appropriate evaluation of "A" and "D" by a location correlating means, such as a data processing section within computer 45, can provide a resultant comparison datum which represents the amount by which the process is out of registration. For example, if the OB marker area arrives at the cutter two counts later than when it should arrive, then "A" would be two counts higher and "D" two counts lower. The comparison datum may be referred to as a "set point error", which can be determined in accordance with the following formula:

Set Point Error = $(A - D)/2$

The set point error described above has a built-in robustness that should be mentioned. If for some reason the gain of the detector increases, then the area "A" would increase in size. Similarly, the area "D" would also increase by approximately the same amount. The set point error value would, however, remain substantially unchanged.

Note that the first edge of the UV detector signal in FIG. 10 represents the first edge of the patch. The first edge of the fiber optic signal, such as from infrared sensor 84, also represents the same patch edge. The differences between these two signal edges can arise from the effects of various factors, such as the gain adjustments and the spatial distance between the two sensors. With respect to the shown embodiment of the invention, this difference is referred to as "sensor offset". Each time a new set of signals are received, a running average of this sensor offset is calculated and saved for the calculation of set point error, which is described in the next-section.

Another quantity that facilitates the calculation of the set point error is the width of the patch. It has been established that the first edge of the UV signal in FIG. 10 is an edge of the patch. It is clear that the last edge of the signal represents the other edge of the patch. The difference of the two signal edges is the width of the patch. In a particular aspect of the invention, a running average of this patch width measurement can also be kept up to date.

Figure 11:
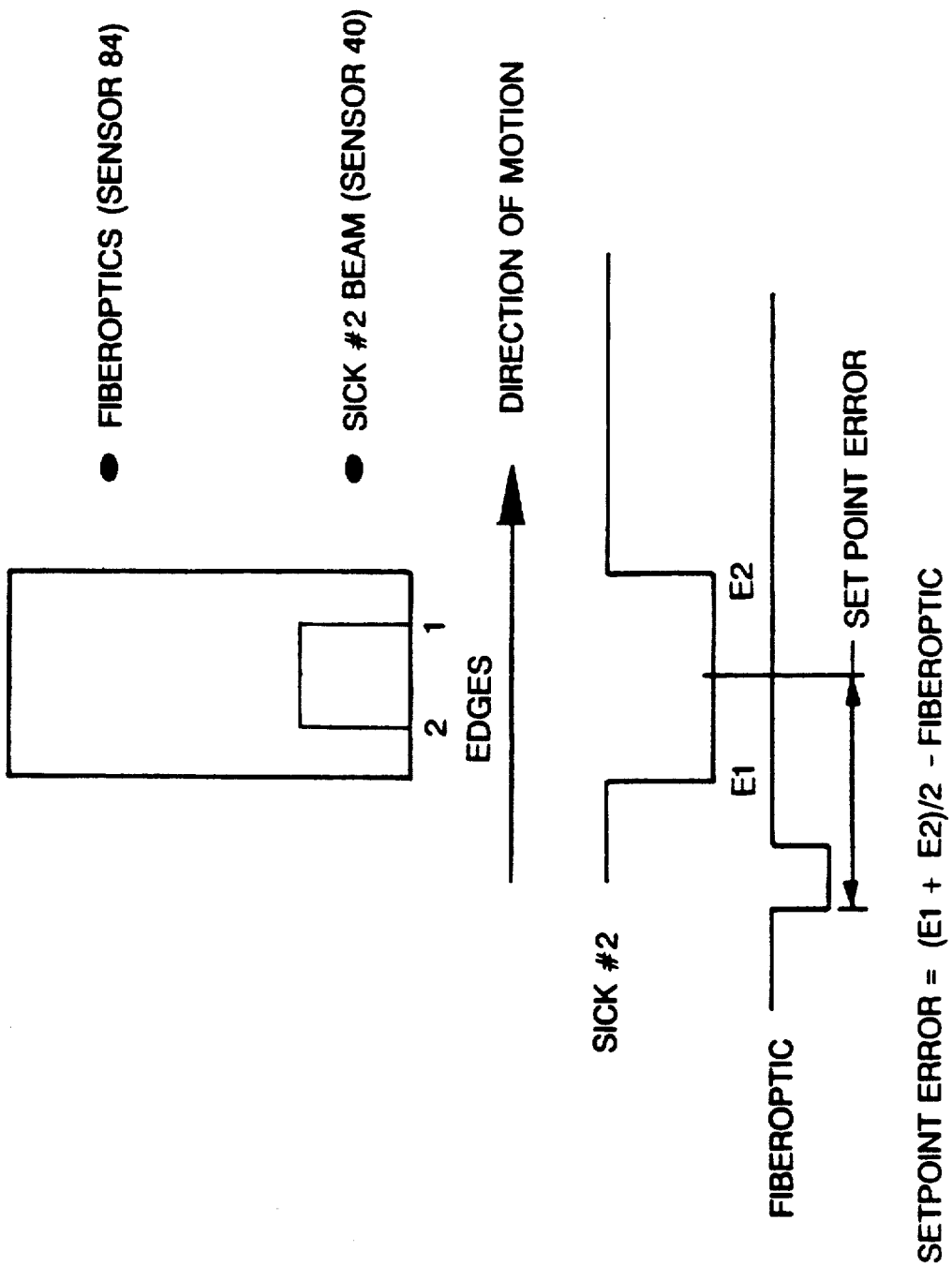
FIG. 11 representatively shows a web segment patch with one (e.g. whole) reference marker portion thereon, and representatively shows corresponding signal pulses generated in response thereto.

After a new roll of web material is spliced in to the manufacturing line, the cutting process can become sufficiently out of registration to leave a complete OB mark on a single patch. FIG. 11 representatively shows the appearance of such a patch with the associated sensor signals. It is readily apparent that the first edge of the UV signal no longer represents an edge of the patch. To determine the cut position relative to the OB mark, the position of the edge of the patch is required. On the basis of the first edge of the fiber optic signal from sensor 84 and the "sensor offset" described above, the position of the first edge of the patch can be estimated. By adding a number value corresponding to the patch length 96 to the first edge, one can obtain an estimate of the position of the second edge of the patch. Note that the center of the OB mark, estimated by the average of the two UV sensor signal edges, is the point where the cut needs to be for ideal registration. Note also that the first edge of the patch represents a knife position. The set point error, therefore, is the difference between the first patch edge and the center of the OB mark as shown in FIG. 11.

The second edge of the patch also represents a knife position which can also be used to estimate the set point error. The only significant difference between the two is that one signifies "need to advance" and the other "need to retard". The estimation procedure used in this application estimates both quantities and chooses one, using their magnitudes and previous values as criteria.

The Set Point Error can be employed to generate a new, updated set point value in accordance with the following formula:

$$\text{New Set Point} = \frac{1}{N} \left[ \sum_{i=1}^{N} (E_i + D_{i-k}) \right]$$

Where:

N = moving average sample size, number of patches (in the shown embodiment, for example, N = 32).

E = set point error, expressed in number of counts for patch "i".

$D_{i-k}$ = registration data from buffer expressed in number of counts (e.g. see FIG. 8) for patch "i-k".

k = number of patches ordinarily located in transit between cut location 33 and sensor 40.

i = selected patch.

As previously mentioned, the set reference value corresponds to the target value plus the set point value. Accordingly, an updated set point value will result in an updated set reference value. It is, therefore, readily apparent that whenever the present specification describes a new or updated set point value, the specification is also describing a new or updated set reference value.

The present invention can further incorporate an Invalid Sensor Offset system. This system can, for example, be activated when the set point and sensor offset are not yet valid due to the absence of previous information. Erroneous signals may also cause the sensor offset to be occasionally incorrect and thereby activate the system. When a complete OB mark is on a patch, the set point error calculation processing sequence has a feature that requires the set point error to have a predetermined, large magnitude of at least ½ the length 70 of an OB mark. This will cause the set point of the registration control loop to move in relatively large increments, and shorten the time in which the OB mark will be cut into two fragments. Once the cutter is cutting through the OB mark, the set point error using the formula, (A − D)/2, will adjust the set point in smaller increments to an appropriate value. The sensor offset will also be updated to a correct value after the OB mark is cut. Note that when the Invalid Sensor Offset system is operating, the control system may not be as responsive as the case when the sensor offset is correct, but it does provide an improved avenue by which the invention can find a correct registration when the manufacturing line is first being started up.

Gear Ratio

The phase regulating means of the invention can be assisted by a gear-ratio control means for selectively adjusting a relative speed at which the web material is provided by the supplying means. More particularly, the relative speed can represent a comparison between the web speed of web material 22 and a line speed of substrate material 36.

The gear ratio can be calculated by the VME unit comprising computer 45. The gear ratio particularly refers to the number of encoder counts from drive motor encoder 82 occurring per web segment patch length 96 (FIG. 6), divided by the number of the number of encoder counts from reference encoder 77 occurring per article length 51 (FIG. 1). In the shown embodiment, for example, sensor 24 is configured to send one pulse per OB mark, motor encoder 82 turns 2.5 revolutions per patch length, and reference encoder 77 turns one revolution per article length 51. Accordingly, the gear ratio can be represented by the number of encoder counts from motor encoder 82 between successive pulse signals from sensor 24, divided by the number of encoder counts per revolution of reference encoder 77. If, for example, one considers that motor encoder 82 and reference encoder can each give 10000 ppr (pulses per revolution) in the "quadrature" mode of the dual-axis card of DCS 49 (2500 pulses×4), motor encoder 82 would move 25000 counts between pulses from sensor 24, and in the same period, the reference encoder would move one turn, or 10000 counts. Therefore, the ratio would be 25000/10000=2.5.

The schematically shown dual-axis (2-axis) card is part of the DCS unit, and is used to control the position of the servo motor 80. Whenever the motor turns, an associated encoder 82 on it sends position data to a 2-axis card as well as the VME computer unit 45 for the gear ratio calculation. The 2-axis card is configured in a gearing mode, and uses the input from a second reference encoder 77 connected to the cutter unit for position data which indicates what the rest of the machine is doing. For every turn of the reference encoder on the cutter unit, which is mechanically geared to turn once per diaper length 51, the 2-axis card sends a move command to the Reliance HR2000 motor driver to move motor 80 according to the gear ratio.

Figure 12:
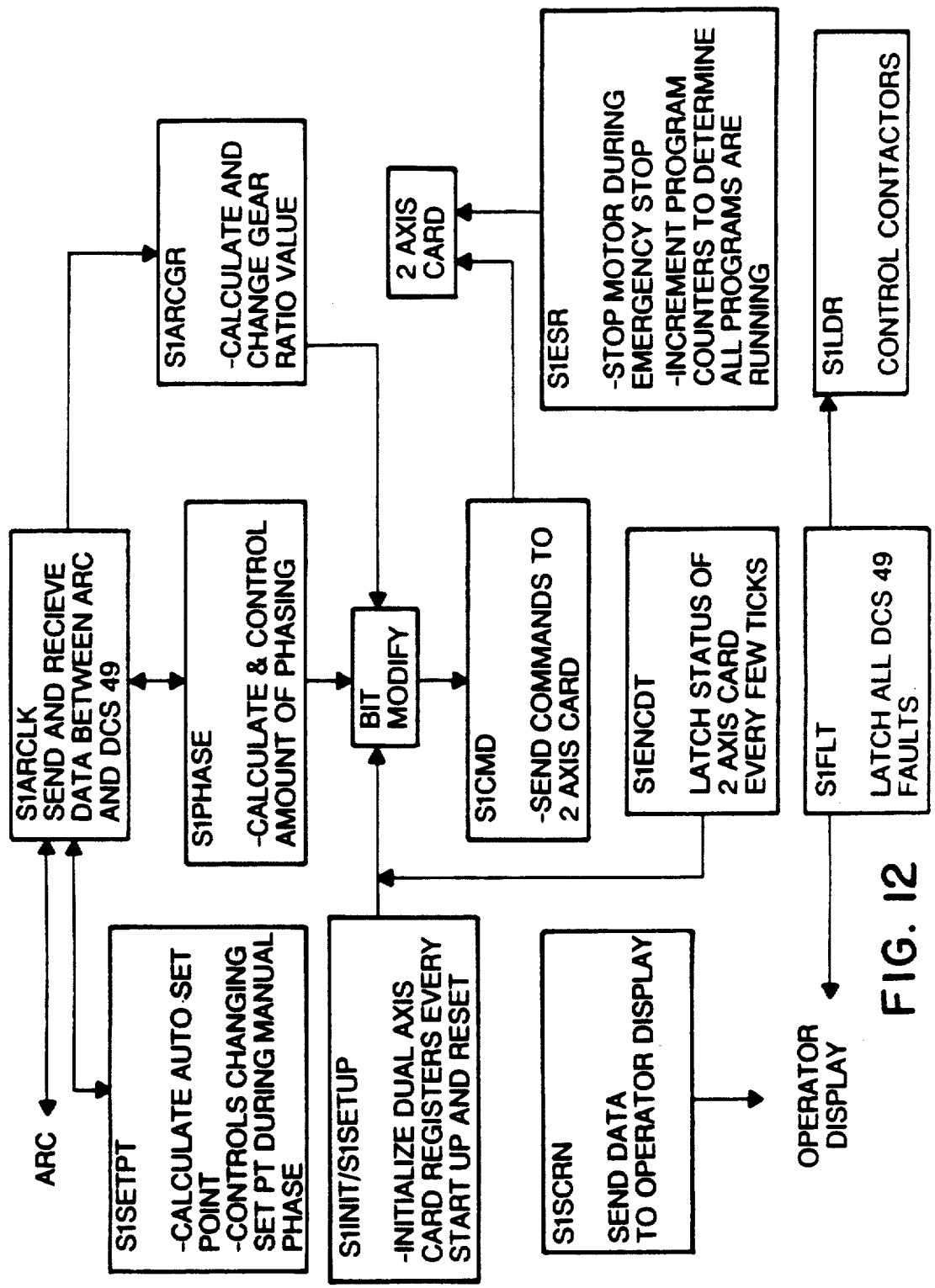
FIG. 12 representatively shows a block diagram of the process control mechanism employed by the present invention.
Figure 13:
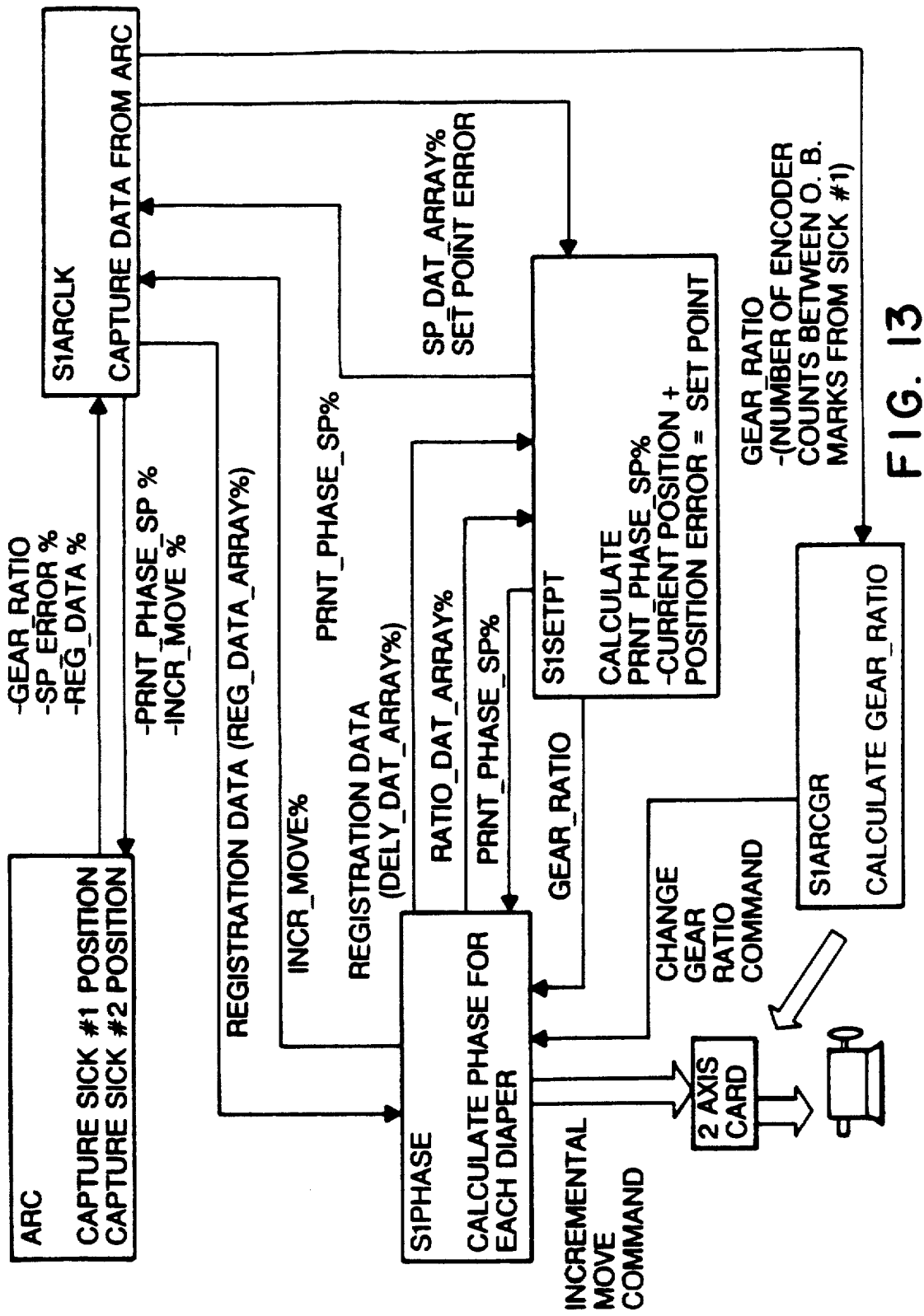
FIG. 13 representatively shows a more detailed block diagram of control system of the invention.

FIG. 12 generally shows the processing sequences or programs which are employed to carry out various functions. The programs that are employed in the control scheme are representatively diagrammed in FIG. 13. The automatic registration control (ARC) capability of computer 45 plays an important part in the control scheme, and the computer operably sends GEAR RATIO data, set point error data (SP_ERROR %), and registration data (REG_DATA %) to DCS 49 across suitable transmission means, such as RS422 communication cables.

DCS 49 in turn sends the set point (PRNT_PHASE_SP) and incremental move (INCR_MOVE %; amount of advance or retard) to computer 45 which, because of its interrupt speed capabilities, can be used to implement automatic registration control (ARC). It can quickly compute the positions and locations which correspond to the signals received from the various sensors, as well as compute other necessary data. DCS 49 receives this data and distributes it through SLARCLK, which is receives and sends data to the various subsystem programs for further processing. SLARCGR is used to average the data from computer 45 and to change the gear ratio if necessary. SIPHASE calculates how much to phase motor 80 based on the registration data. Finally, SISETPT calculates and updates the set point using registration data and set point error data. As representatively shown in FIG. 13, all of these subsystems work together to ultimately get the information to the 2-axis card so that it can accurately control the motor.

As previously discussed, even if the web segment patches change size, the physical distance between the detector and the knife is always the same. As a result, motor 80 must physically turn a substantially constant number of times to move a patch (e.g. reference marker) from sensor 24 to the knife and cutting location 33. The number of turns is related to a certain number of encoder pulses. The number of pulses that are received by the invention can be used to predict where the OB marker and its associated web segment patch are going to be when the web material is cut by the knife. From this information, motor 80 can be sped up or slowed down, as required to properly position the OB marker relative to the knife cut.

Figure 14:
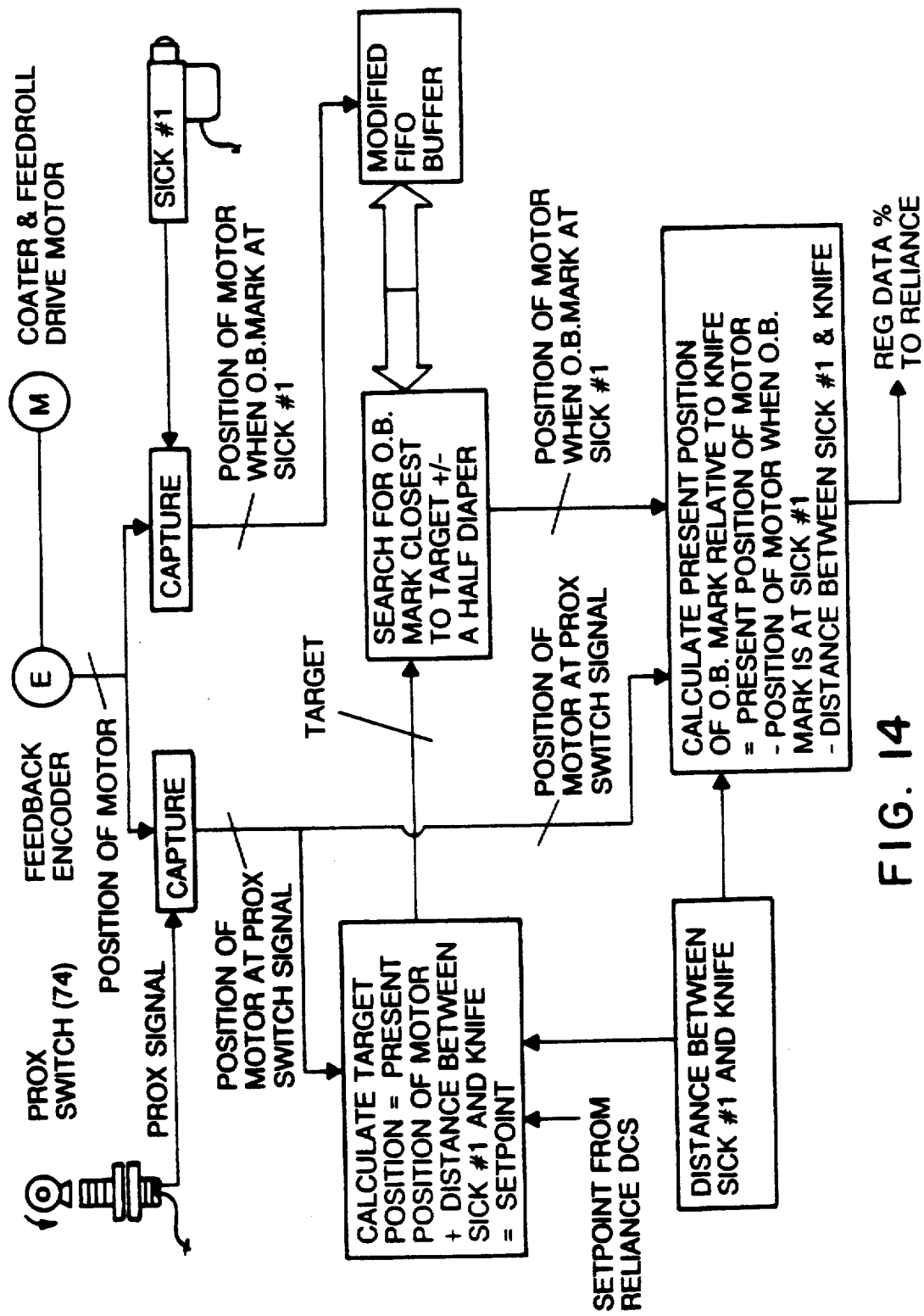
FIG. 14 representatively shows a block diagram of the pitch distance compensation, phase adjustment aspect of the invention.

FIG. 14 representatively shows a block diagram of the improved "pitch distance compensation" provided by the present invention. This technique can effectively control the phase position of a web segment patch at the knife even though the knife might be located 20-30 patch lengths from sensor 24. The control can be accomplished even if the patch size changes. For example, the patch size could change because of web stretch.

Each time a sensor 24 pulse is received, the current position of the motor encoder is put into a buffer. Each time a proximity signal is received from proximity switch 74, computer 45 can calculate which value should be found in the buffer. This is done by taking the position of the motor at which the proximity signal came in. The motor position value is added to the distance (in encoder counts) between sensor 24 and the knife. This distance can correspond to a parameter which may be inputted by an operator and displayed on a monitor screen. The parameter, for example, can be inputted in terms of a whole number of web segments. Finally, the set point is added to the previously summed value. This provides the number of encoder counts that should have passed by as the patch moved from sensor 24 to the knife plus the current position. (Since the counter decrements for each motor encoder pulse, the addition of the numbers in the manner described above should provide the number in the buffer that was put in X web segments ago, where X is the number of web segment lengths from sensor 24 to the knife). Having the "target value" for the particular system configuration and the number of positions to look back in the buffer, the processing sequence can find the actual value of the counter when the diaper passed sensor 24. This value is compared to the target value and the difference is found. The difference is added to the set point and sent to DCS 49 as a registration datum.

The processing system SIPHASE subtracts off the set point from this number and phases the motor the correct amount. Processing system SISETPT adds the set point error onto this value and computes a new, updated set point.

FIG. 15 provides an example of a buffer searching sequence. In the shown embodiment of the invention, the counter is configured to count down. For the sake of easier understanding, however, the example of FIG. 15 employs a counter which is counting up. The value of a counter is put into a buffer each time an OB mark passes under sensor 24 (the detector looking at the web material before it is cut). Each time a proximity signal is received from proximity switch 74 mounted on the cutting mechanism, the system recognizes that the knife is about to make its next cut and that a new web segment patch is arriving at the cutter. The system then chooses the appropriate value to be taken out of the buffer. For a particular machine set up, the number of entries looked back in the buffer corresponds to the physical number of web segment patches between sensor 24 (SICK #1) and the knife. The operator enters this number into the system, and the number may also be displayed on monitor screen 86. In the shown example, the "Target Encoder Counts to Travel" corresponds to the Gear Ratio (2.4) times the number of Pulses Per Revolution of Encoder 82 (2500 Accordingly, the value "6000" was derived from the calculation (2.4) * (2500). It should be noted that computer 45 in this example does not employ a quadrature mode.

When there is an error between where a patch should be at the knife and where it actually is, the following phasing control scheme is used. If large errors are found, the correction is made immediately. An error of over 1 millimeter is considered large. When smaller error differences are calculated, however, the differences are integrated until their sum is greater than the 1 millimeter mark. This sum is then averaged, and the appropriate amount of advance or retard is made. With reference to the example illustrated by FIG. 16, a set point value of 4000 counts is assumed, and there is first a difference of −10 counts. When this error is added to the following error of +10 counts, the accumulation is zero. The processing sequence does nothing for this situation. Looking down the example, however, the accumulated error eventually does exceed a predetermined value. At this point, the accumulation is averaged, and a phase correction, incremental move is made. Only when the accumulated error reaches a given level does any correction take place. This is one method of implementing integral control.

Figure 17:
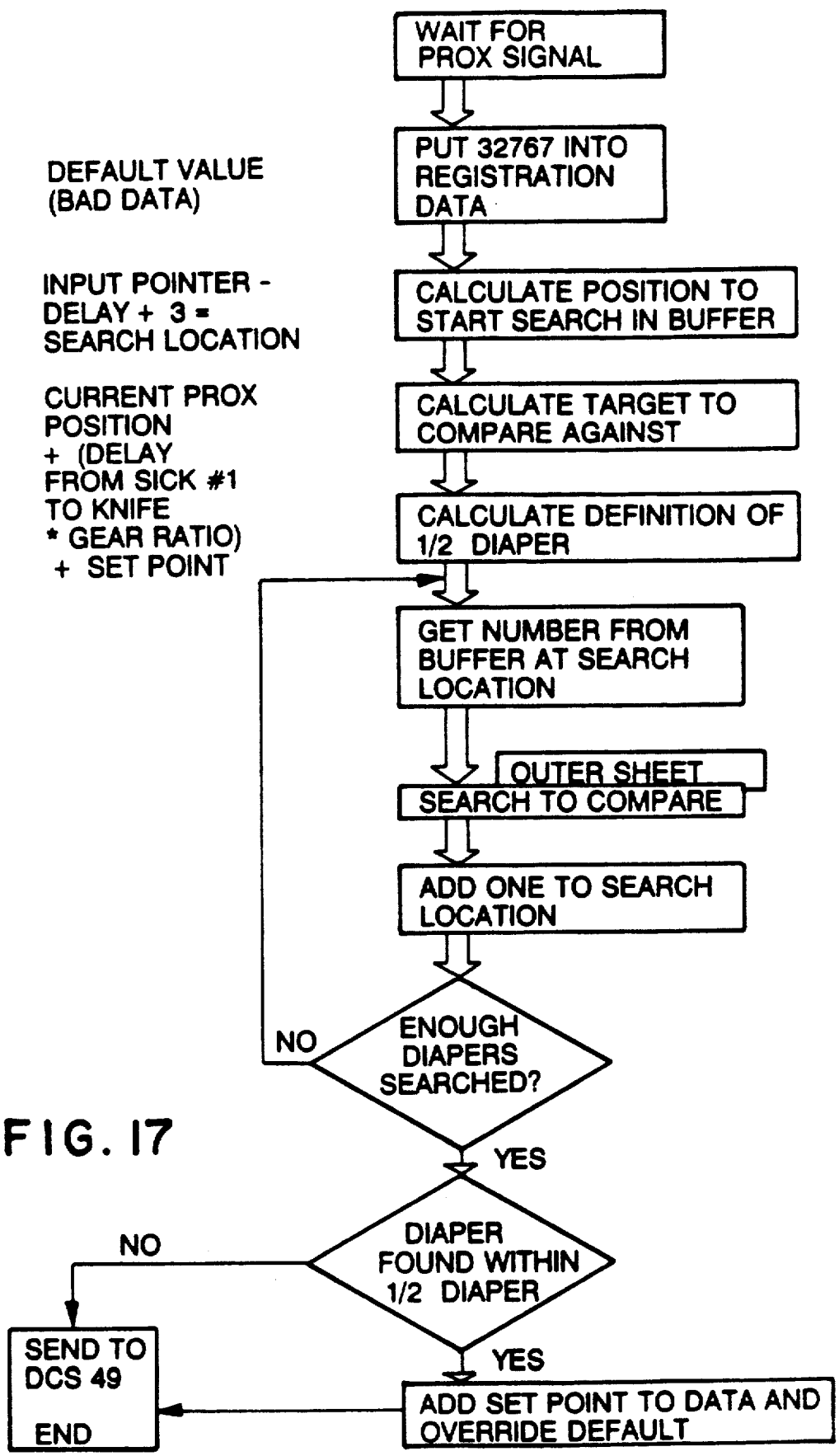
FIG. 17 representatively shows a flow diagram of the buffer searching process employed phase adjustment mechanism of the invention.
Figure 18:
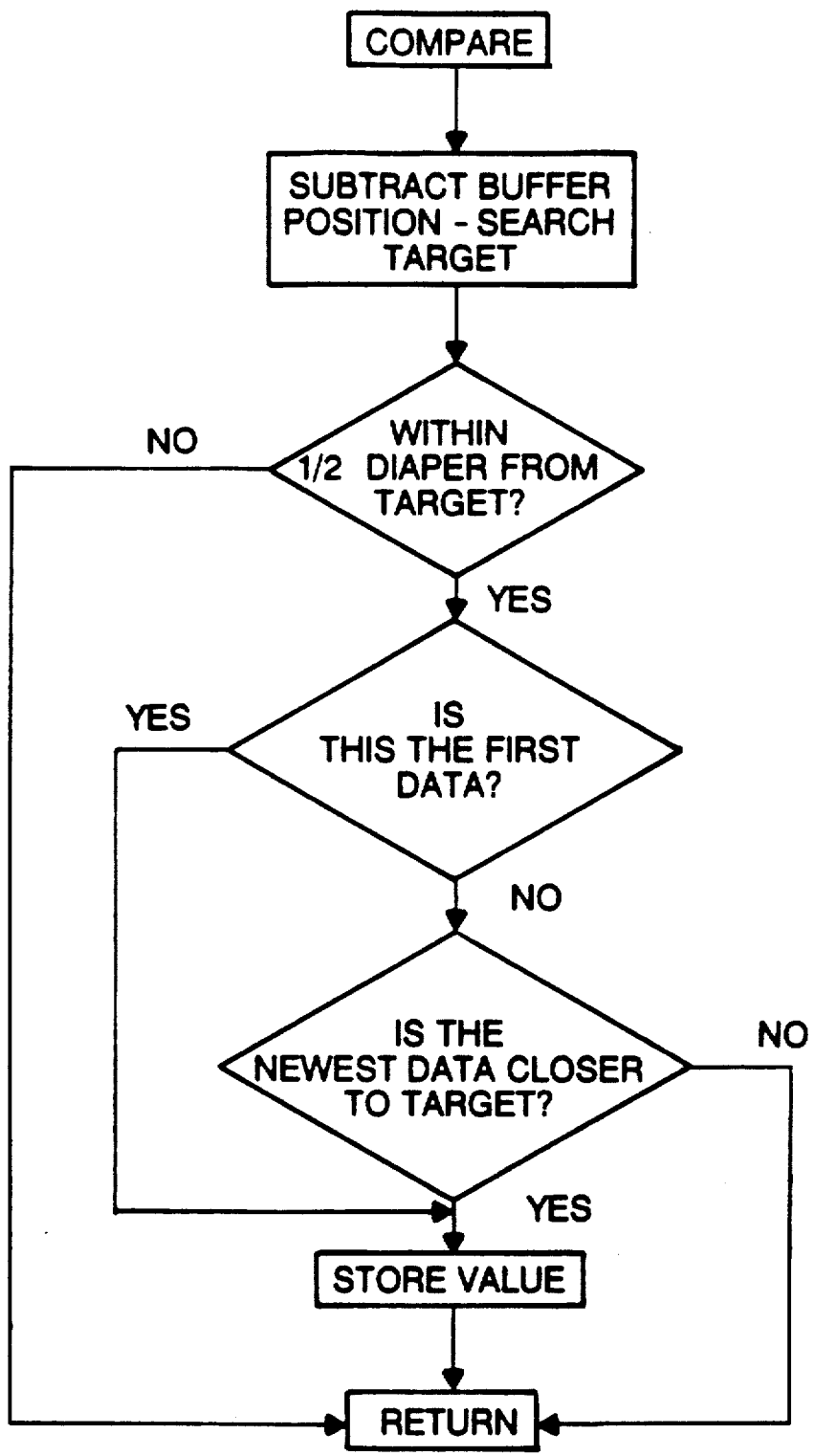
FIG. 18 representatively shows a more detailed flow diagram of the "compare" process employed by the invention.

FIGS. 17 and 18 representatively show the processing sequence that searches the data buffer for the data corresponding to patch arriving at the knife for the next cutting operation. Every sensor 24 pulse the encoder counter value is captured and put into a memory array/buffer, and a pointer is incremented. In a particular embodiment, the actual buffer is 64 positions long. Each new entry overwrites the oldest entry in the buffer. This overwrite processing sequence is not shown.

FIGS. 17 and 18 illustrate the processing sequence for utilizing data from the buffer. As mentioned earlier, data is taken out of the buffer every time a signal is received from proximity switch 74. The main processing sequence is interrupted, and the buffer processing sequence will run on that signal. Once the processing sequence begins execution, it puts a default value into the registration register. If no data is found in the buffer that matches the criteria, a default value, such as 32767, is sent to indicate bad or missing data. The next step is to calculate where to begin searching in the buffer. To do this the processing sequence looks at the pointer for the processing sequence that is putting data into the buffer. It then counts back from this point the number of web segments from sensor 24 to the knife. That position should be where the data is found. However, there is no way of knowing if extra, erroneous sensor 24 pulses were generated. For this reason, the shown embodiment of the invention searches the entire buffer to find the appropriate value. The processing sequence calculates the number that it expects to find in the buffer. This calculation was explained earlier with reference to FIG. 14.

With reference to FIG. 17, the definition of half a web segment is calculated next. The term, half of a web segment, corresponds to one-half of the number of encoder counts from encoder 82 that are generated per web segment (patch) length.

Each of the numbers in the buffer within the search range are taken out and sent to the "compare" subroutine. This subroutine, as representatively shown in FIG. 18, looks at each of the numbers sent to it and picks the best one that is within half a web segment from the target value. If a valid number value is not found, the default value is not overwritten and the default value is sent to DCS 49. If a valid number value is found when the compare routine is finished, the set point is added to the difference between the number value and the target value. The resultant number is sent to DCS 49.

Figure 19A:
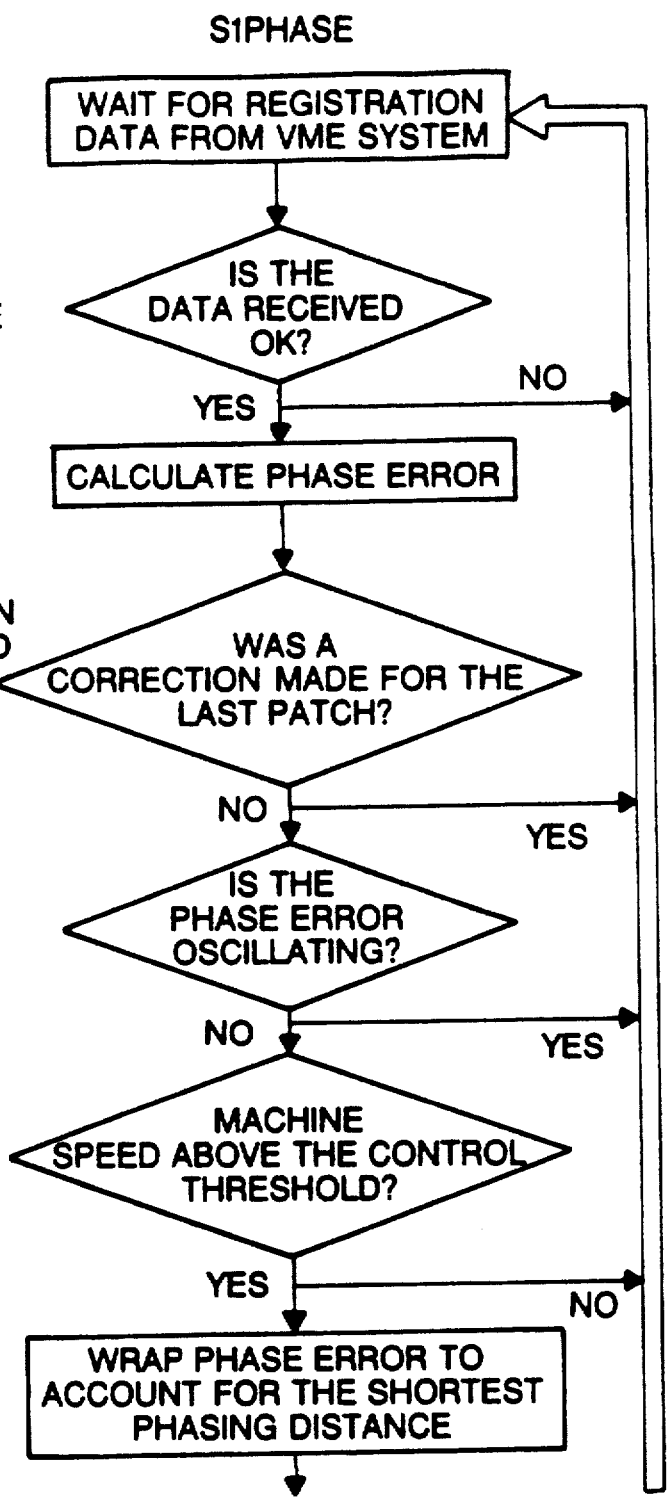
FIGS. 19A and 19B representatively show a flow diagram of the process for determining position (phase) error per web segment patch.
Figure 19B:
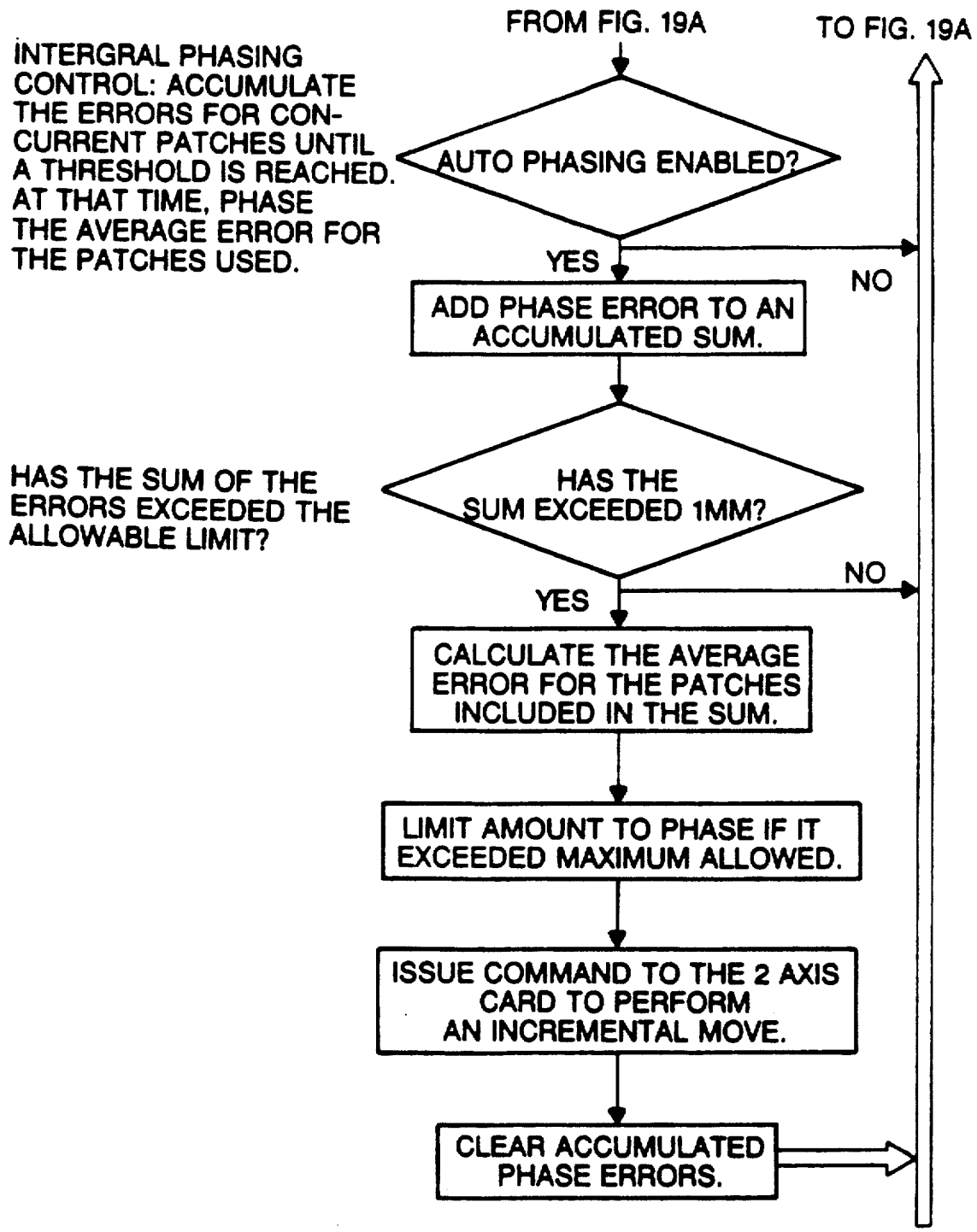

FIGS. 19A and 19B show a flow chart which represents the processing system (SLPHASE) for calculating the position (phase) error with respect to the desired cutting location for each web segment patch. The registration data for the web segment patch at the cutting knife is sent t-o DCS 49 from the VME unit, computer 45. The registration data is verified to check that it is within a range of reasonable values. The registration data is compared to the current set point value and a phase error is calculated. The processing system then checks to determine whether or not a phase correction had been made for the last web segment patch. This helps to improve the accuracy of the processing system because communication delays may cause the data collected immediately after a phase correction to be inaccurate. To further determine the accuracy of the phase error data, the system checks to see if the phase error data has become erratic or is otherwise unstable. In addition, the processing system checks to see if the machine line speed is above a minimum speed. The phase error data is then wrapped to determine the shortest phasing distance.

The term, "wrapped" or "wrapping", refers to a processing step which is similar to the "modulus function" in mathematics. The modulus function returns the remainder when two numbers are divided. For example: 7000 mod 6000 = 1000. When the technique of the invention is calculating desired parameters, such as set point value or amount of incremental phasing, sections of data corresponding to one or more whole web segment (patch) lengths can be removed from consideration. The wrapping function removes the section of data which corresponds to one or more whole patch lengths from a number value, and leaves only a remainder value which corresponds to a fraction of a patch length. For example, if the technique of the invention determines that an incremental phasing of 1.2 patch lengths is required, the 1.2 value is wrapped back, or has the modulus function performed on it, to provide an actual incremental phasing of 0.2 patch length. In addition, the technique of the present invention can advantageously determine and execute the shortest path for the incremental phasing. For example, if the invention determines that an incremental phasing advance of 0.7 patch length is required, the invention will provide an incremental phasing retard of 0.3 patch length to produce the equivalent result with a lesser net amount of actual adjustment to the process line. The selected smaller amounts of adjustment can advantageously reduce the reaction time and increase the corrective speed of the invention.

Figure 20A:
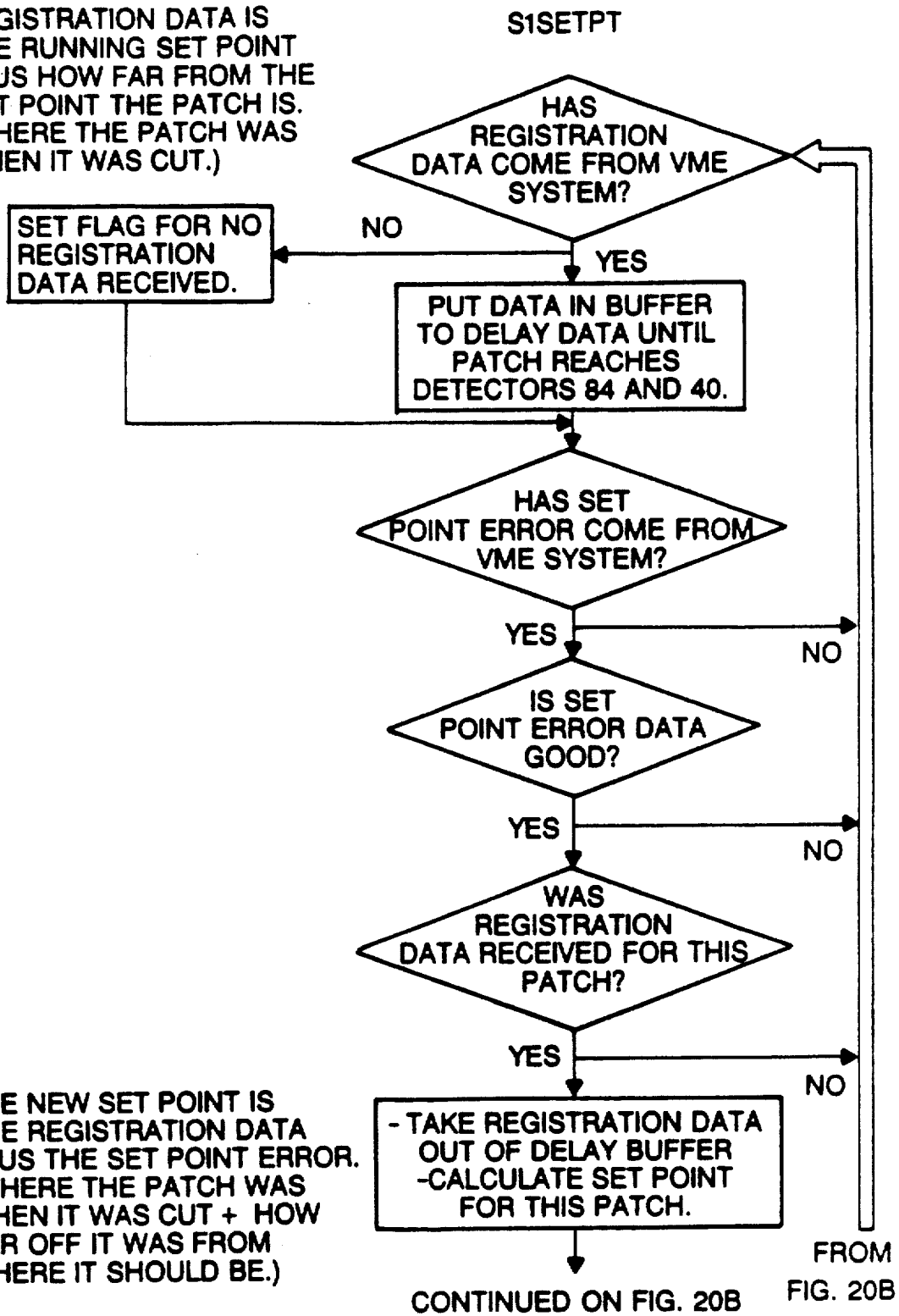
FIGS. 20A and 20B representatively show a flow diagram of the process for automatically determining the updated set point value employed by the invention.
Figure 20B:
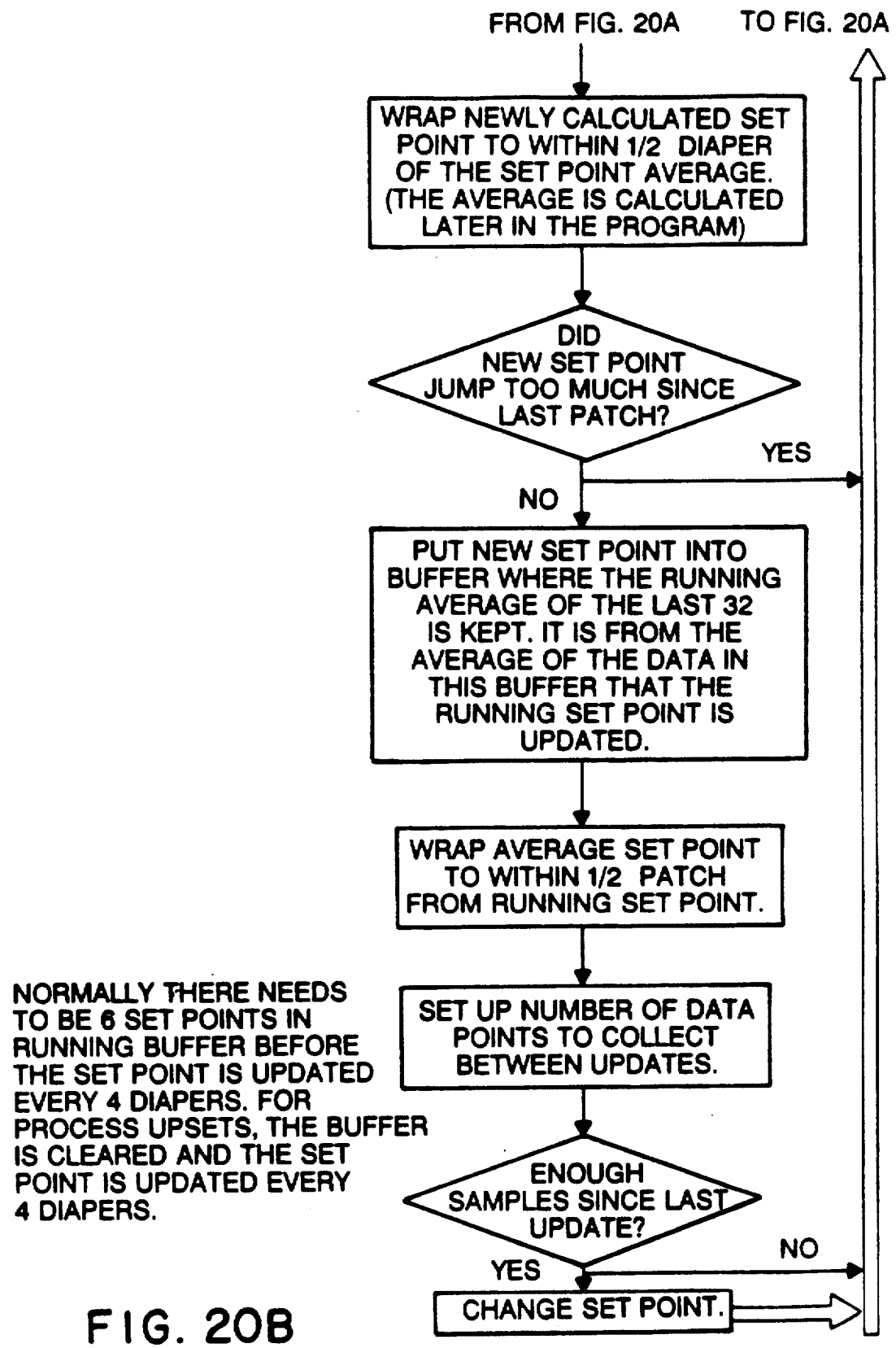

Since the shown embodiment of the invention employs integral phasing control, the phasing error data are accumulated until a threshold value is teached. In the illustrated embodiment, the threshold is set at 1 millimeter. Upon reaching the threshold, the average phase error is calculated. The phasing error may be limited to a maximum value, which in the illustrated embodiment is about one-fourth of a patch length. Upon determining the desired amount of phasing, a coma nd is issued to the 2-axis card to perform an incremental move. FIGS. 20A and 20B show a flow chart which represents the automatic set point system (SISETPT) of the invention. To automatically determine an updated set point value, the processing system employs registration data, which comprises the current set point value plus the phasing error for each patch. The registration data for each patch is placed into a buffer to delay the data until the particular patch reaches sensors 84 and 40. When the patch reaches sensors 84 and 40, the sensors provide the signals for determining the set point error for the patch. The set point error data is appropriately verified and then matched with the proper registration data from the buffer. For each web segment patch, the system then calculates a new set point datum which substantially corresponds to the registration datum plus the set point error datum for the patch. The newly calculated set point datum is wrapped to within one-half diaper of the set point average (which is calculated later in the processing system). Each new set point datum is verified and then placed into the set point buffer. Employing the data from the set point buffer, a new set point value is calculated employing the formula set forth elsewhere in the present description. Once determined, the new set point value can be employed by the phase regulating means of the present invention.

Figure 21:
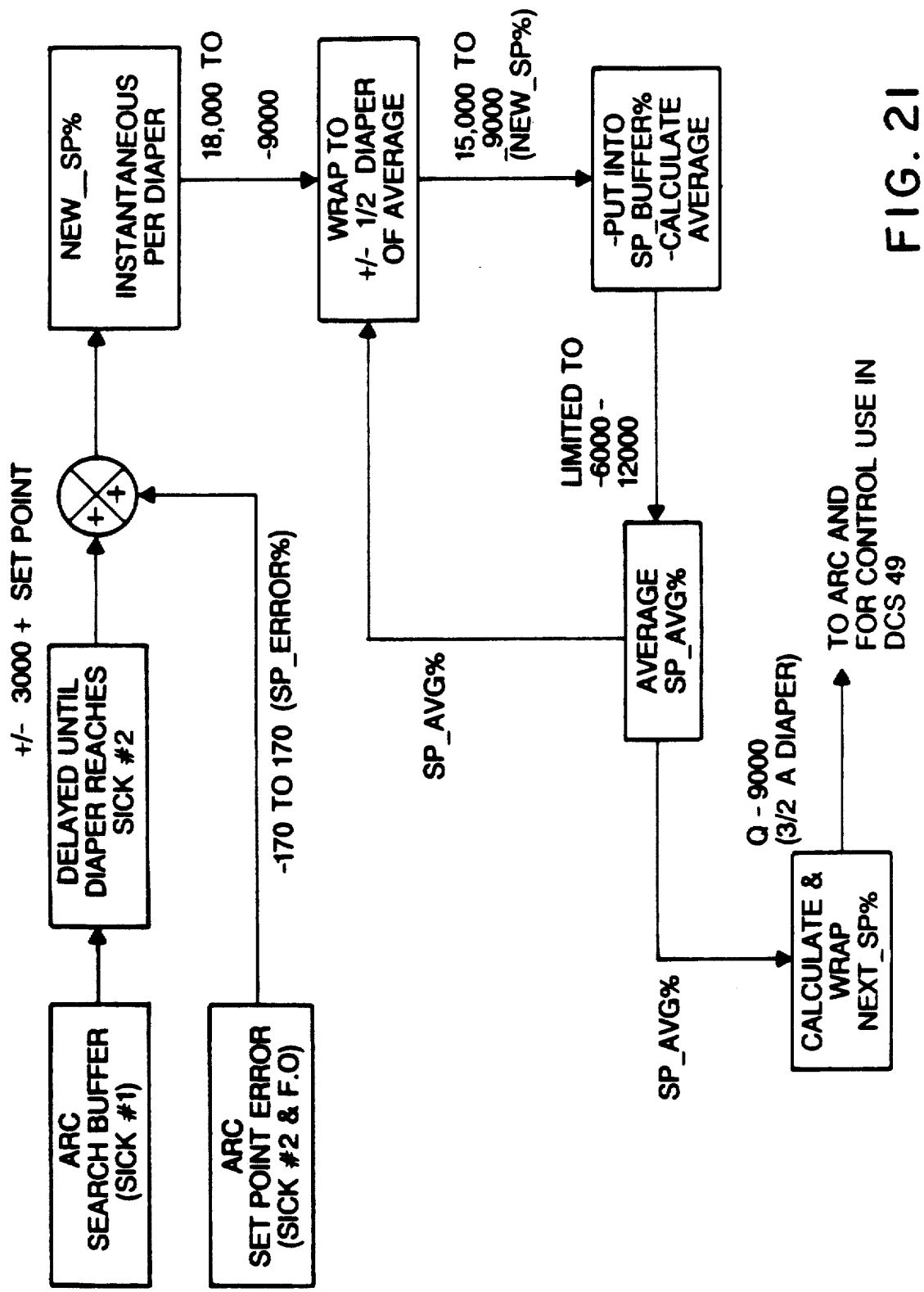
FIG. 21 representatively shows a diagram which illustrates the flow of data employed in the "automatic set point" aspect of the invention.

FIG. 21 pertains to the calculation of data for automatic set point updating. With reference to the upper left of FIG. 21, the registration data from sensor 24 is summed with set point error from sensor 40 and the fiber optic detector 84. The latter two detectors are mounted after the cutter unit, and give feedback indicating how well the cut was made. In other words, the two detectors show the amount of inaccuracy in the current set point value (set point error). The registration data is the set point plus the error in position from the target. The registration data effectively represents the actual position the patch was at when the patch was cut. When this position is added to how far off this position is, the NEW_SP % is created. This is the set point the web segment that just passed would have needed to be cut exactly correct. For every web segment, a NEW_SP %, is created. This value is put into a set point buffer (SP_BUFFER %) after it is "wrapped" to within ½ a web segment from the average. (Wrapping is a unique function. Since there are approximately 6000 encoder pulses per web segment patch, a value of 9000 and 3000 can both indicate the center of the patch; the difference being that the first value is the middle of a patch offset by a whole patch.) As each new value is put into the buffer, the oldest value is removed. The shown embodiment of the invention, for lo example, only keeps the last 32 values in the buffer. The set point buffer is similar to the buffer used for storing registration data in computer 45. The running average (SP_AVG %) of the web segments in the buffer is calculated. This value is sent to NEXT_SP % and is wrapped to within 3/2 of a web segment (approximately 0-9000). This value is then sent to computer 45 and used in DCS 49 for control.

FIG. 22 illustrates a further aspect of the invention pertaining to the mechanism by which the set reference regulating means of the invention can automatically update the set point from data in the buffer. As representatively shown, a running average of the data in the set point buffer is constantly updated every web segment. The running set point, however, is not updated every web segment. In a particular embodiment of the invention, the set point buffer is 32 web segments long, and whenever the buffer is cleared, it must wait for BIG_UPDATE % web segments to be placed in the buffer. Once this happens, every SMALL_UPDATE % web segments into the buffer will cause the set point to change. In a particular embodiment, for example, BIG_UPDATE % can be set to 6, and SMALL_UPDATE % can be 4 by default.

A splice, such as a splice between a new roll of web material and an expiring roll of web material, is a special case, however. When a splice occurs, counters inside the processing sequences can be employed to indicate when the splice reaches sensors 40 and 84 after the knife. At this time, the set point buffer is cleared. After SMALL_UPDATE % number of web segments have corresponding data values stored in the buffer, the set point is updated every SMALL_UPDATE % number of web segment samples. This operating arrangement will allow the set point to change rapidly during a very dynamic period in the process.

For every web segment a corresponding set point is calculated. This number is put into a buffer where a running average is kept. The shown embodiment, for example, keeps a running average of the last 32 values. In addition, during normal running conditions, an average value determined from every four web segments is used to continually update the current set point. As a result, the system is able to react quickly-to process upsets and can rapidly change the set point when needed. Ordinarily, no operator inputs are needed after the initial operating parameters are set up.

The gear ratio is the number of turns of the motor for every turn of the reference encoder 77. The gear ratio data used by DCS 49 is collected in computer 45. Computer 45 calculates the ratio by counting the number of motor encoder counts between sensor 24 pulses and dividing by 10000.

Figure 23A:
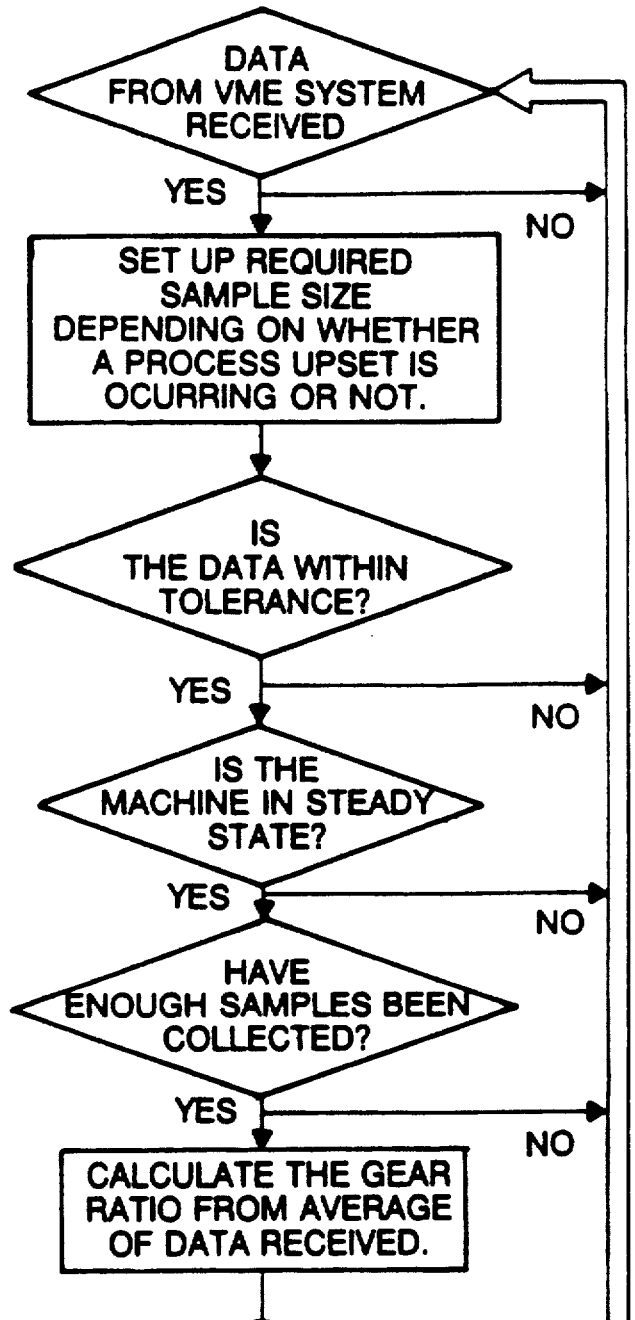
FIG. 23A and 23B representatively show a flow diagram of the process for determining the updated gear ratio value employed by the invention.
Figure 23B:
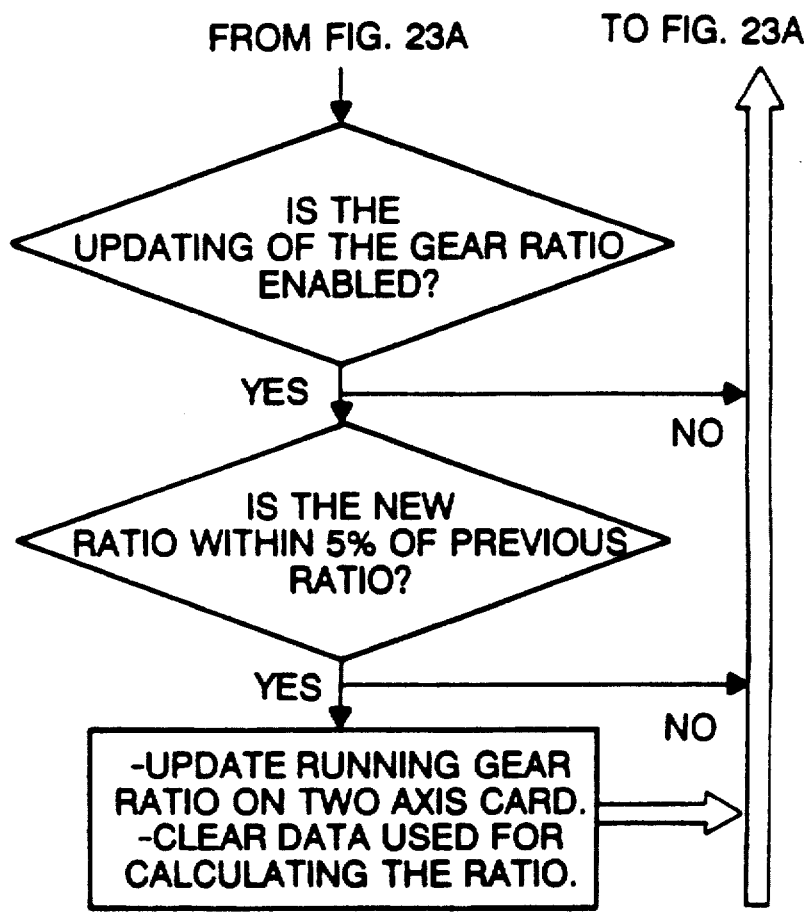

FIGS. 23A and 23B show a flow chart which represents the gear ratio updating system (S1ARCGR) of the invention. The gear ratio updating system of the present invention receives from VME unit, computer 45, data which comprises the number of encoder counts between signal pulses provided by sensor 24. The number of encoder counts between signal pulses from sensor 24 corresponds to an individual web segment patch on-web material 22. In a preferred embodiment of the invention, the number of web segment lengths (sample size) depends upon whether or not the apparatus is suffering a process upset, such as a web splice. The gear ratio data are then verified and an appropriate sample size of gear ratio data are averaged to generate an updated gear ratio value. The new gear ratio is verified and sent to the 2-axis card of DCS 49 to appropriate control the speed of motor 80.

Figure 24:
FIG. 24 representatively shows an example of a preferred method for determining the gear ratio value.

With reference to the illustrative example shown in FIG. 24, it is assumed that each of the two encoders 82 and 77 produce 10000 ppr (pulses per revolution) and that sensor 24 sends one pulse per OB mark. If motor 80 needs to turn 2.5 times to mechanically move one web segment patch, then it moves 25000 counts between sensor 24 pulses. In the same period, the reference encoder moves one turn, or 10000 counts (the reference encoder is mechanically geared to turn once per diaper length). Accordingly, the gear ratio can be calculated as follows: $25000/10000 = 2.5$.

FIG. 25 refers to a second technique of calculating the gear ratio. DCS 49 processing sequences do calculate a gear ratio by employing this technique, but it is only calculated as a way of visually monitoring the accuracy of method described in FIG. 24. In the technique illustrated in FIG. 25, the number of encoder pulses for the reference encoder and the motor encoder that occur in a given amount of time are determined. These two values are each put in a sum of previously collected values. When enough samples are collected, the two sums are divided and the gear ratio is obtained. The example assumes that the time for each sample is approximately the length of time for one revolution of the reference encoder (10,000 ppr). In the same time the motor travels 24,000 pulses. When these two numbers are divided, a gear ratio is produced.

As discussed with respect to the automatic set point portion of the invention, the gear ratio may be calculated differently during a major process upset, such as the upset produced by a splice between rolls of material. In particular, during normal running conditions, the number of encoder pulses between sensor 24 signals can be averaged over a relatively larger number of web segments, and during a major process upset, such as a web splice, such number of encoder pulses can be averaged over a relatively smaller number of web segments. For example, the gear-ratio aspect of the invention can be configured such that during normal running conditions, the number of encoder pulses between sensor 24 signals can be averaged over approximately 25 web segments. When a splice passes sensor 24, the invention can be configured to determine an updated gear ratio while taking an average from every 5–10 web segments. This aspect of the invention can allow the gear ratio processing sequence to respond better to changes in the process.

Having thus described the invention in rather full detail, it will be readily apparent that various changes and modifications can be made without departing from the spirit of the invention. All of such changes and modifications are contemplated as being within the scope of the invention, as defined by the subjoined claims.

We claim:

1. An article, comprising:
   a backsheet layer;
   a substantially liquid permeable topsheet layer disposed in an adjacent facing relation with said backsheet layer;
   an absorbent pad sandwiched between said topsheet and backsheet layers; and
   a relatively smaller patch of web material secured to an inward or outward facing surface of said backsheet layer, said patch having thereon at least one reference marker portion and a predetermined set of graphics which is congruously entire, said reference marker portion constructed to provide for a selected separating of said predetermined set of graphics from an interconnected plurality of graphic sets.

* * * * *